(12) United States Patent
Kashmiri et al.

(10) Patent No.: US 7,569,673 B2
(45) Date of Patent: Aug. 4, 2009

(54) HUMANIZED ANTI-TAG 72 CC49 FOR DIAGNOSIS AND THERAPY OF HUMAN TUMORS

(75) Inventors: Syed V. S. Kashmiri, Gaithersburg, MD (US); Jeffrey Schlom, Potomac, MD (US); Eduardo A. Padlan, Kensington, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 251 days.

(21) Appl. No.: 10/519,580

(22) PCT Filed: Jun. 26, 2003

(86) PCT No.: PCT/US03/20367

§ 371 (c)(1),
(2), (4) Date: Jul. 11, 2005

(87) PCT Pub. No.: WO2004/003155

PCT Pub. Date: Jan. 8, 2004

(65) Prior Publication Data

US 2006/0165680 A1 Jul. 27, 2006

Related U.S. Application Data

(60) Provisional application No. 60/393,077, filed on Jun. 28, 2002.

(51) Int. Cl.
| | | |
|---|---|---|
| *C12P 21/08* | (2006.01) | |
| *C07K 16/00* | (2006.01) | |
| *G01N 33/574* | (2006.01) | |
| *A61K 39/395* | (2006.01) | |
| *C07H 21/04* | (2006.01) | |

(52) U.S. Cl. .............. 530/387.3; 424/133.1; 424/141.1; 424/155.1; 424/178.1; 435/7.23; 435/69.6; 435/70.21; 530/388.1; 530/388.8; 530/391.3

(58) Field of Classification Search ........................ None
See application file for complete search history.

(56) References Cited

U.S. PATENT DOCUMENTS

| | | | |
|---|---|---|---|
| 4,816,567 | A | 3/1989 | Cabilly et al. |
| 5,472,693 | A | 12/1995 | Gourlie et al. |
| 5,482,040 | A | 1/1996 | Martin, Jr. |
| 5,512,443 | A | 4/1996 | Schlom et al. |
| 5,534,254 | A | 7/1996 | Huston et al. |
| 5,585,089 | A | 12/1996 | Queen et al. |
| 5,688,657 | A | 11/1997 | Tsang et al. |
| 5,976,531 | A | 11/1999 | Mezes et al. |
| 5,976,845 | A | 11/1999 | Mezes et al. |
| 5,994,511 | A | 11/1999 | Lowman et al. |
| 6,054,297 | A | 4/2000 | Carter et al. |
| 6,180,370 | B1 | 1/2001 | Queen et al. |
| 6,495,137 | B1 | 12/2002 | Mezes et al. |
| 7,081,518 | B1 * | 7/2006 | Pastan et al. ............. 530/387.3 |

FOREIGN PATENT DOCUMENTS

| | | |
|---|---|---|
| CA | 2131355 | 4/2001 |
| CA | 2068593 | 7/2003 |
| EP | 0239400 | 9/1987 |
| EP | 0365997 | 5/1990 |
| WO | WO 89/00692 | 1/1989 |
| WO | WO 89/01783 | 5/1989 |
| WO | WO 90/04410 | 5/1990 |
| WO | WO 91/00295 | 1/1991 |
| WO | WO 93/12231 | 6/1993 |
| WO | WO 96/13594 | 5/1996 |
| WO | WO 97/26010 | 7/1997 |
| WO | WO 98/18809 | 5/1998 |
| WO | WO 99/43816 | 2/1999 |
| WO | WO 00/26394 | 5/2000 |

OTHER PUBLICATIONS

Iwahashi et al. Molecular Immunology, 1999. 36:1079-1091.*
Paul, Fundamental Immunology, 3rd Edition, 1993, pp. 292-295.*
Rudikoff et al. Proc. Natl. Acad. Sci. USA, 79:1979-1983, Mar. 1982.*
Colman. Research in Immunology, 145:33-36, 1994.*
Bendig M. M. Methods: A Companion to Methods in Enzymology, 1995; 8:83-93.*
MacCallum et al. J. Mol. Biol., 262, 732-745, 1996.*
Casset et al. Biochemical and Biophysical Research Communications, 307:198-205, 2003.*
Abergel et al., "Crystallographic Studies and Primary Structure of the Antitumor Monoclonal CC49 Fab'," *Proteins: Structure, Function, and Genetics* 17:438-443, 1993.
Colcher et al., "Radioimmunolocalization of Human Carcinoma Xenografts with B72.3 Second Generation Monoclonal Antibodies," *Cancer Research* 48:4597-4603, Aug. 15, 1988.
De Pascalis et al., "Grafting of "abbreviated" complementarity-determining regions containing specificity-determining residues essential for ligand contact to engineer a less immunogenic humanized monoclonal antibody," *J. Immunol.* 169:3076-3084, 2002.

(Continued)

*Primary Examiner*—David J. Blanchard
(74) *Attorney, Agent, or Firm*—Klarquist Sparkman, LLP.

(57) ABSTRACT

The present disclosure provides humanized CC49 monoclonal antibodies that bind TAG-72 with high binding affinity and that are minimally immunogenic. In one embodiment, a humanized CC49 antibody includes a non-conservative amino acid substitution in a light chain complementarity determining region 3 of the CC49 antibody. In a further embodiment, the humanized CC49 antibody includes a non-conservative substitution of a first residue in a light chain complementarity determining region 3 and a substitution of a second residue in a complementarity determining region of the humanized CC49 antibody. In several of the embodiments, methods are disclosed for the use of a humanized CC49 antibody in the detection or treatment of a tumor in a subject. Also disclosed is a kit including the humanized CC49 antibody described herein.

49 Claims, 9 Drawing Sheets

OTHER PUBLICATIONS

De Pascalis et al., "In vitro affinity maturation of a specificity-determining region-grafted humanized anticarcinoma antibody: isolation and characterization of minimally immunogenic high-affinity variants," *Clin. Can. Res.* 9:5521-5531, 2003.

Divgi et al., "Clinical Comparison of Radiolocalization of Two Monoclonal Antibodies (mAbs) Against the TAG-72 Antigen," *Nucl. Med. Biol.* 21(1):9-15, 1994.

Gonzales et al., "Minimizing immunogenicity of the SDR-grafted humanized antibody CC49 by genetic manipulation of the framework residues," *Mol. Immunol.* 40:337-349, 2003.

Hakimi et al., "Reduced immunogenicity and improved pharmacokinetics of humanized anti-Tac in cynomolgus monkeys," *J. Immunol.* 147:1352-1359, 1991.

Hand et al., "Potential for Recombinant Immunoglobulin Constructs in the Management of Carcinoma," *Cancer Supplement* 73(3):1105-1113, Feb. 1, 1994.

Iwahashi et al., "CDR substitutions of a humanized monoclonal antibody (CC49): contributions of individual CDRs to antigen binding and immunogenicity," *Mol. Immunol.* 36:1079-1091:1999.

Johnson et al., "Analysis of a Human Tumor-associated Glycoprotein (TAG-72) Identified by Monoclonal Antibody B72.3," *Cancer Research* 46:850-857, Feb. 1986.

Jones et al., "Replacing the Complementarity-determining Regions in a Human Antibody with those from a Mouse," *Nature* 321:522-525, May 29, 1986.

Kashmiri et al., "Generation, characterization, and in vivo studies of humanized anticarcinoma antibody CC49," *Hybridoma* 14(5):461-473, 1995.

Kashmiri et al., "Development of a minimally immunogenic variant of humanized anti-carcinoma monoclonal antibody CC49," *Crit. Rev. Oncol. Hematol.* 38:3-16, 2001.

Kashmiri et al., Chapter 21 in *Methods in Molecular Biology*, vol. 248: *Antibody Engineering: Methods and Protocols*, p. 361-376; Lo (ed.), Humana Press, Inc., Tolowa, NJ, 2003.

Mulligan et al., "Phase I Study of Intravenous $^{177}$Lu-labeled CC49 Murine Monoclonal Antibody in Patients with Advanced Adenocarcinoma," *Clinical Cancer Research* 1:1447-1454, Dec. 1995.

Muraro et al., "Generation and Characterization of B72.3 Second Generation Monoclonal Antibodies Reactive with the Tumor-associated Glycoprotein 72 Antigen," *Cancer Research* 48:4588-4596, Aug. 15, 1988.

Padlan, "A Possible Procedure for Reducing the Immunogenicity of Antibody Variable Domains while Preserving their Ligand-binding Properties," *Molecular Immunology* 28(4/5):489-498, 1991.

Padlan, "Anatomy of the antibody molecule," *Mol. Immunol.* 31:169-217, 1994.

Padlan et al., "Identification of Specificity-determining Residues in Antibodies," *The FASEB Journal* 9:133-139, Jan. 1995.

Paul, *Fundamental Immunology*, Raven Press, NY, Ch. 8, p. 242, 1993.

Reichman et al., "Reshaping human antibodies for therapy," *Nature* (London) 332:323-327, 1988.

Rixon et al., "Preferential Use of a H Chain V Region in Antitumor-associated Glycoprotein-72 Monoclonal Antibodies," *The Journal of Immunology* 151(11):6559-6568, Dec. 1, 1993.

Rudikoff et al., "Single amino acid substitution altering antigen-binding specificity," *Proc Natl Acad Sci U S A*. March; 79(6): 1979-1983, 1982.

Saldanha et al., "A single backmutation in the human kIV framework of a previously unsuccessfully humanized antibody restores the binding activity and increases the secretion in cos cells," *Mol. Immunol.* 36:709-719, 1999.

Schier et al., "Isolation of picomolar affinity anti-c-erbB-2 single-chain Fv by molecular evolution of the complementarity determining regions in the center of the antibody binding site," *J. Mol. Biol.* 263:551-567, 1996.

Sha et al., "A heavy-chain grafted antibody that recognizes the tumor-associated TAG72 antigen," *Cancer Biother.* 9(4):341-349, 1994.

Sharkey et al., "Evaluation of a complementarity-determining region-grafted (humanized) anti-carcinoembryonic antigen monoclonal antibody in preclinical and clinical studies," *Cancer Res.* 55:5935s-5945s, 1995.

Slavin-Chiorini et al., "Biological properties of chimeric domain-deleted anticarcinoma immunoglobulins," *Cancer Res.* 55(23 Suppl.):5957s-5967s, 1995.

Slavin-Chiorini et al., "A CDR-grafted (humanized) domain-deleted antitumor antibody," *Cancer Biother. Radiopharm.* 12:305-316, 1997.

Tamura et al., "Structural correlates of an anticarcinoma antibody: identification of specificity-determining residues (SDRs) and development of a minimally immunogenic antibody variant by retention of SDRs only," *J. Immunol.* 164:1432-1441, 2000.

Wu et al., "Humanization of a murine monoclonal antibody by simultaneous optimization of framework and CDR residues," *J. Mol. Biol.* 294:151-162, 1999.

Xiang et al., "The tyrosine residue at position 97 in the VH CDR3 region of a mouse/human chimeric anti-colorectal carcinoma antibody contributes hydrogen bonding to the TAG72 antigen," *Cancer Biother.* 8:253-262, 1993.

Xiang et al., "Complementarity determining region residues aspartic acid at H55, serine at H95 and tyrosines at H97 and L96 play important roles in the B72.3 antibody-TAG-72 antigen interaction," *Protein Eng.* 9:539-543, 1996.

Xiang et al., "Light-chain framework region residue Tyr71 of chimeric B72.3 antibody plays an important role in influencing the TAG72 antigen binding," *Protein Eng.* 12:417-421, 1999.

Adams and Schier, "Generating improved single-chain Fv molecules for tumor targeting," *Journal of Immunological Methods*, 231(1-2):249-260, 1999.

De Pascalis et al., "In Vitro Affinity Maturation of a Specificity-Determining Region-Grafted Humanized Anticarcinoma Antibody: Isolation and Characterization of Minimally Immunogenic High-Affinity Variants," *Clinical Cancer Research*, 9(15):5521-5531, 2003.

Osbourn et al., "Generation of a panel of related human scFv antibodies with high affinities for human CEA," *Immunotechnology*, 2(3):181-196, 1996.

Supplementary Partial European Search Report issued on Feb. 27, 2006, for European Patent Application No. EP03762161.2.

* cited by examiner

FIG. 1

| | 27b | | | 91 | |
|---|---|---|---|---|---|

A. CC49

| | Leu | | | | Tyr | |
|---|---|---|---|---|---|---|

B. HuCC49V10

| | Val | | | | Tyr | |
|---|---|---|---|---|---|---|

C. HuCC49V14

| | Val | | | | Pro | |
|---|---|---|---|---|---|---|

D. HuCC49V15

| | Leu | | | | Pro | |
|---|---|---|---|---|---|---|

LCDR1　　　　　　　　　　　LCDR3 pComb3H-SS

FIG. 6

Sample ID: HuIgG

| Marker | % Gated | % Total | Mean |
|---|---|---|---|
| All | 100.00 | 92.37 | 3.54 |
| M1 | 99.71 | 92.10 | 3.49 |
| M2 | 0.31 | 0.29 | 20.51 |

Sample ID: cCC49 1ug

| Marker | % Gated | % Total | Mean |
|---|---|---|---|
| All | 100.00 | 44.81 | 41.60 |
| M1 | 27.25 | 12.21 | 5.92 |
| M2 | 73.04 | 32.73 | 54.78 |

Sample ID: HuCC49 1ug

| Marker | % Gated | % Total | Mean |
|---|---|---|---|
| All | 100.00 | 85.59 | 18.04 |
| M1 | 70.78 | 60.58 | 4.36 |
| M2 | 29.43 | 25.19 | 50.88 |

Sample ID: HuCC49-V10 1ug

| Marker | % Gated | % Total | Mean |
|---|---|---|---|
| All | 100.00 | 87.85 | 15.56 |
| M1 | 72.35 | 63.56 | 4.46 |
| M2 | 27.81 | 24.43 | 44.41 |

Sample ID: HuCC49-7 1ug

| Marker | % Gated | % Total | Mean |
|---|---|---|---|
| All | 100.00 | 87.77 | 15.79 |
| M1 | 71.22 | 62.51 | 4.35 |
| M2 | 28.87 | 25.34 | 44.00 |

Sample ID: HuCC49-12 1ug

| Marker | % Gated | % Total | Mean |
|---|---|---|---|
| All | 100.00 | 88.55 | 14.46 |
| M1 | 73.53 | 65.11 | 4.31 |
| M2 | 26.62 | 23.57 | 42.47 |

Sample ID: HuCC49-14 1ug

| Marker | % Gated | % Total | Mean |
|---|---|---|---|
| All | 100.00 | 87.02 | 24.54 |
| M1 | 56.44 | 49.11 | 5.40 |
| M2 | 43.76 | 38.08 | 49.17 |

Sample ID: HuCC49-15 1ug

| Marker | % Gated | % Total | Mean |
|---|---|---|---|
| All | 100.00 | 80.62 | 33.47 |
| M1 | 32.20 | 25.96 | 6.29 |
| M2 | 68.07 | 54.88 | 46.23 |

FIG. 7
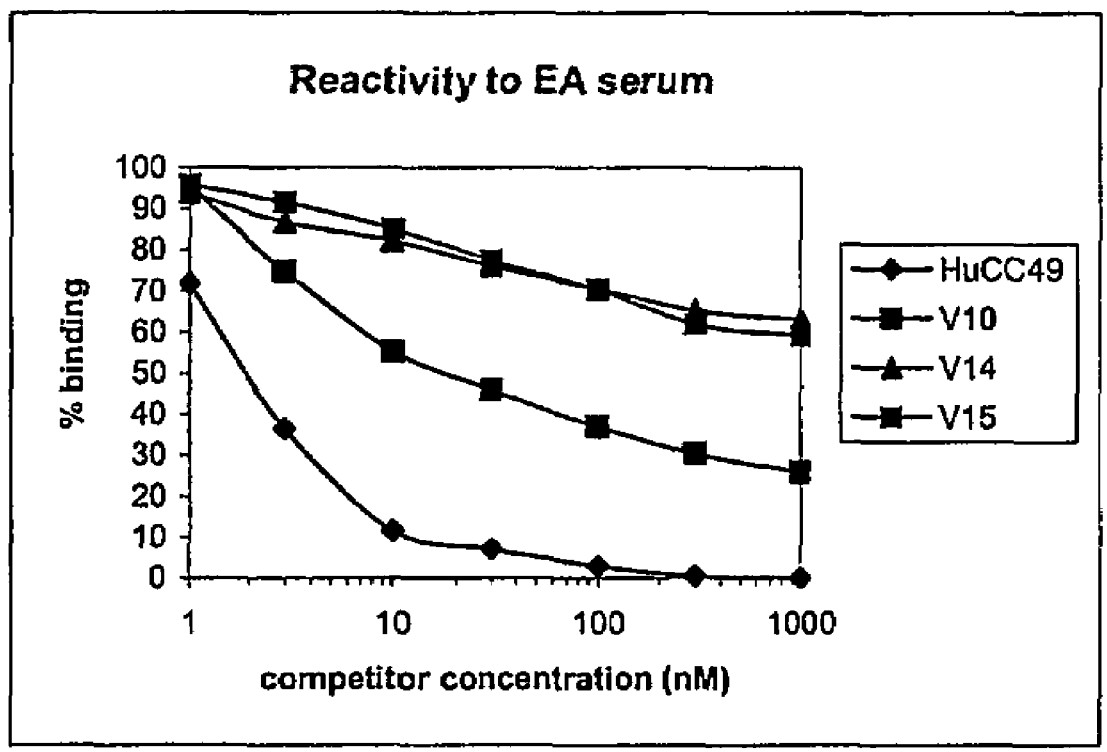
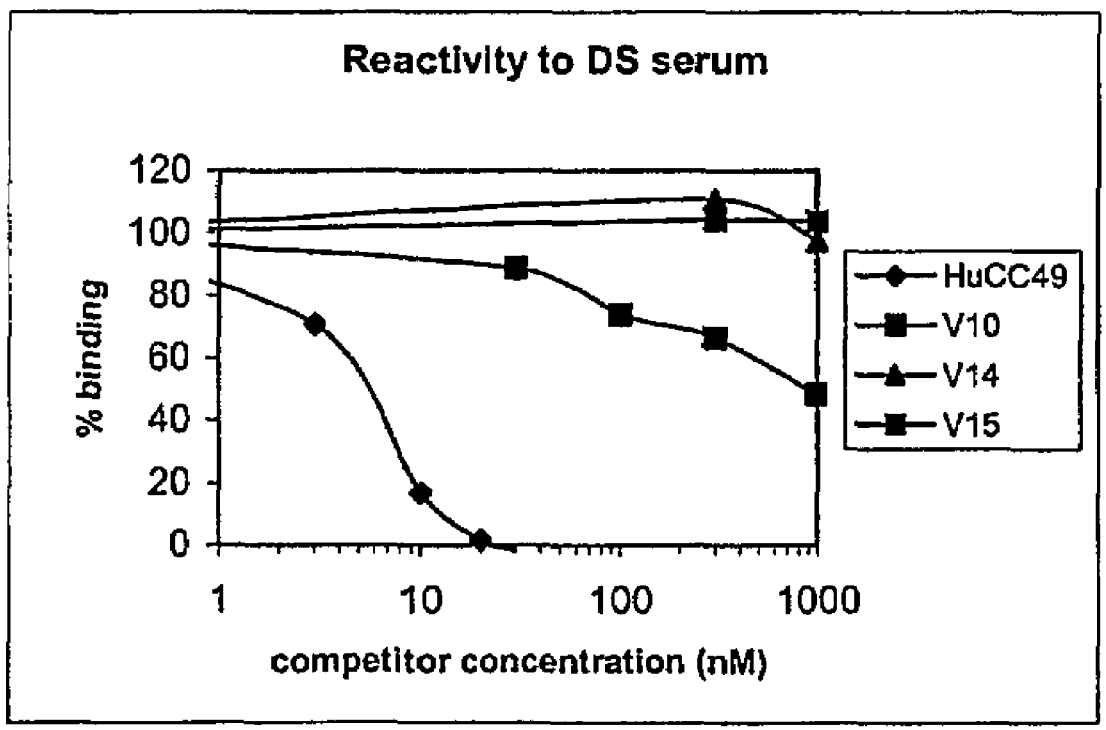

US 7,569,673 B2

HUMANIZED ANTI-TAG 72 CC49 FOR DIAGNOSIS AND THERAPY OF HUMAN TUMORS

PRIORITY CLAIM

This is the § 371 U.S. National Stage of International Application No. PCT/US2003/020367, filed Jun. 26, 2003, which was published in English under PCT Article 21(2), which in turn claims the benefit of U.S. Provisional Application No. 60/393,077, filed Jun. 28, 2003, which is incorporated herein by reference.

FIELD

The present disclosure relates to humanized monoclonal antibodies that bind a tumor antigen. More specifically, the present disclosure relates to humanized monoclonal antibodies with non-conservative amino acid substitutions that have a high binding affinity for tumor-associated glycoprotein (TAG)-72 and minimal immunogenicity.

BACKGROUND

The use of murine monoclonal antibodies in medicine has significant potential especially in the diagnosis and treatment of various diseases, including cancer. The advantage of using monoclonal antibodies resides in their specificity for a single antigen. A monoclonal antibody raised against a specific tumor cell surface antigen can be coupled to therapeutic agents, such as radioisotopes and chemotherapeutic drugs, and these immunoconjugates can be used clinically to specifically target, for example, a tumor cell of interest.

A major limitation in the clinical use of monoclonal antibodies is the development of a human anti-murine antibody (HAMA) response in the patients receiving the treatments. The HAMA response can involve allergic reactions and an increased rate of clearance of the administered antibody from the serum. Various types of modified monoclonal antibodies have been developed to minimize the HAMA response while trying to maintain the antigen binding affinity of the parent monoclonal antibody. One type of modified monoclonal antibody is a human-mouse chimera in which a murine antigen-binding variable region is coupled to a human constant domain (Morrison and Schlom, *Important Advances in Oncology*, Rosenberg, S. A. (Ed.), 1989). A second type of modified monoclonal antibody is the complementarity determining region (CDR)-grafted, or humanized, monoclonal antibody (Winter and Harris, *Immunol. Today* 14:243-246, 1993).

The tumor-associated glycoprotein (TAG)-72, is expressed on the cells of a majority of human carcinomas, including adenocarcinoma, colorectal, gastric, pancreatic, breast, lung and ovarian carcinomas. Murine monoclonal antibodies have been disclosed that specifically bind TAG-72. One of these antibodies, CC49, has been shown to efficiently target and reduce the size of human colon carcinoma xenografts in nude mice, and has been targeted to a variety of carcinomas in a number of clinical trials. Unfortunately, the clinical utility of the CC49 monoclonal antibody has been limited because of its murine origin. Thus, there clearly exists a need to develop a humanized CC49 antibody with both high antigen binding affinity and low immunogenicity for use in human subjects.

SUMMARY

The present disclosure relates to humanized CC49 monoclonal antibodies that bind TAG-72 with high binding affinity and that are minimally immunogenic.

In one embodiment of the disclosure, a humanized CC49 antibody includes a non-conservative amino acid substitution in a light chain complementarity determining region 3 of the CC49 antibody, or functional fragment thereof, and has a high binding affinity for TAG-72.

In another embodiment, a humanized CC49 antibody includes a nucleic acid sequence encoding the antibody that is deposited as ATCC Accession number PTA-4182 or ATCC Accession number PTA-4183. ATCC Accession numbers PTA-4182 and PTA-4183 were deposited in the American Type Culture Collection (10801 University Boulevard, Manassas, VA 20110-2209) on Mar. 26, 2002.

In one embodiment, a humanized CC49 antibody with high binding affinity for TAG-72 and minimal immunogenicity includes a variable light framework region and a variable heavy framework region of a human antibody. The humanized CC49 antibody has at least one complementarity determining region from a human antibody and the remaining complementarity determining regions from a murine CC49 antibody. The humanized CC49 antibody also includes a non-conservative substitution of a first residue in a light chain complementarity determining region 3 and a substitution of a second residue in a complementarity determining region of the human CC49 antibody.

Methods are disclosed herein for the use of a humanized CC49 antibody in the detection or treatment of a tumor in a subject. In one specific embodiment, a method is disclosed for detecting a tumor. The method includes contacting a sample obtained from the subject with a humanized CC49 antibody for a sufficient amount of time to form an immune complex, and then detecting the presence of the immune complex. Another method is disclosed for detecting a tumor in a subject that includes administering a humanized CC49 antibody to the subject for a sufficient amount of time to form an immune complex and then detecting the presence of the immune complex. In a further embodiment, a method is disclosed for treating a subject having a tumor that expresses TAG-72. The method includes administering to the subject a therapeutically effective amount of a humanized CC49 antibody, for example, such as an antibody conjugated to a drug or toxin.

A kit is disclosed herein that includes a container with the humanized CC49 antibody described herein.

The foregoing and other features and advantages will become more apparent from the following detailed description of several embodiments, which proceeds with reference to the accompanying figures.

BRIEF DESCRIPTION OF THE FIGURES

FIG. 1 is a schematic drawing comparing amino acid substitutions in CC49, HuCC49V10, HuCC49V10-14 and HuCC49V10-15. Amino acid residue number is shown at the top of the figure. CDR region is indicated at the bottom of the figure.

FIG. 6 is a series of tables of flow cytometric analysis of the binding of CC49 derived recombinant antibodies to Jurkat cells that express TAG-72 antigen on their cell surface. The percent of gated cells for different antibodies are tabulated.

FIG. 7 is a set of graphs demonstrating the reactivity of HuCC49 and its variants to sera from patient EA (FIG. 7A) and DS (FIG. 7B), measured by surface plasma resonance (SPR). Increasing concentrations of the antibodies tested were used to compete with the sera anti-idiotypic (anti variable region) antibodies for binding to HuCC49 immobilized on sensor chip. Percent binding of the sera to HuCC49 was calculated from the sensogram and plotted as a function of the concentration of the competitor.

DETAILED DESCRIPTION

Figure 2:
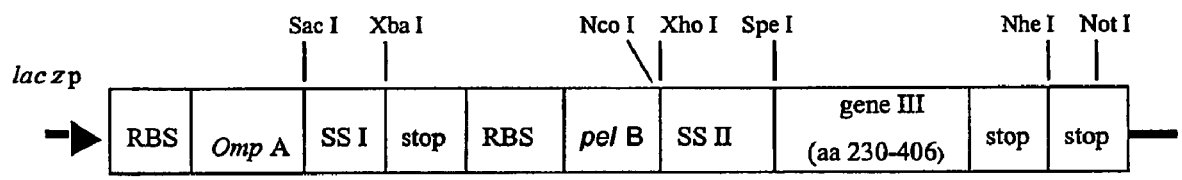
FIG. 2 is a schematic representation of the phage display vector, PComb3H-SS. Only those restriction endonuclease sites are shown that are relevant to cloning of the target genes or converting the expression construct for soluble Fab expression. Gene III indicates a sequence encoding the carboxyl-terminal domain of the gene III protein of phage M13. Lac Z p represents the lac Z promoter of *E. coli*. Omp A and pel B are the prokaryotic leader sequences; RBS shows ribosomal binding site for protein translation. SS I and SS II are the stuffer sequences, and stop denotes the termination codon for protein synthesis.

I. Abbreviations
BSM bovine submaxillary mucin
C constant
CH constant heavy
CL constant light
CDR complementarity determining region
Fab fragment antigen binding
F(ab')$_2$ Fab with additional amino acids, including cysteines necessary for disulfide bonds
FACS fluorescence activated cell sort
FR framework region
Fv fragment variable
H heavy
HAMA human antimurine antibody
HuIgG human immunoglobulin G
Ig immunoglobulin
Ka relative affinity constant
L light
PCR polymerase chain reaction
scFv single chain Fv
SDR specificity determining residue
SPR surface plasmon resonance
TAG-72 tumor associated glycoprotein-72
V variable
VH variable heavy
VL variable light II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: A Comprehensive Desk Reference*, published by VCH Publishers, Inc., 1995 (ISBN 1-56081-569-8).

In order to facilitate review of the various embodiments of the invention, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Antibody: Immunoglobulin (Ig) molecules and immunologically active portions of Ig molecules, i.e., molecules that contain an antigen binding site which specifically binds (immunoreacts with) an antigen. In one embodiment the antigen is tumor-associated glycoprotein (TAG-72). Monoclonal, and humanized immunoglobulins are encompassed by the disclosure. In one embodiment, a murine monoclonal antibody that recognizes the TAG-72 antigen is CC49. In another embodiment, a humanized CC49 antibody is HuCC49. In other embodiments, variant humanized CC49 antibodies are HuCC49V10-14 or HuCC49V10-15. The disclosure also includes synthetic and genetically engineered variants of these immunoglobulins.

A naturally occurring antibody (e.g., IgG) includes four polypeptide chains, two heavy (H) chains and two light (L) chains inter-connected by disulfide bonds. However, it has been shown that the antigen-binding function of an antibody can be performed by fragments of a naturally occurring antibody. Thus, these antigen-binding fragments are also intended to be designated by the term "antibody." Examples of binding fragments encompassed within the term antibody include (i) an Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment (Ward et al., (1989) *Nature* 341:544-546) which consists of a VH domain; and (v) an F(ab')$_2$ fragment, a bivalent fragment comprising two Fab fragments linked by a disulfide bridge at the hinge region. Furthermore, although the two domains of the Fv fragment are coded for by separate genes, a synthetic linker can be made that enables them to be made as a single protein chain (known as single chain Fv (scFv); Bird et al. (1988) *Science* 242:423-426; and Huston et al. (1988) *Proc. Natl. Acad. Sci.* 85:5879-5883) by recombinant methods. Such single chain antibodies, as well as dsFv, a disulfide stabilized Fv (Bera et al. (1998) *J. Mol. Biol.* 281:475-483), and dimeric Fvs (diabodies), that are generated by pairing different polypeptide chains (Holliger et al. (1993) *Proc. Natl. Acad. Sci.* 90:6444-6448), are also included.

In one embodiment, antibody fragments for use in this disclosure are those which are capable of cross-linking their target antigen, e.g., bivalent fragments such as F(ab')$_2$ fragments. Alternatively, an antibody fragment which does not itself cross-link its target antigen (e.g., a Fab fragment) can be used in conjunction with a secondary antibody which serves to cross-link the antibody fragment, thereby cross-linking the target antigen. Antibodies can be fragmented using conventional techniques and the fragments screened for utility in the same manner as described for whole antibodies. An antibody is further intended to include humanized monoclonal molecules that specifically bind the target antigen.

"Specifically binds" refers to the ability of individual antibodies to specifically immunoreact with an antigen. This binding is a non-random binding reaction between an antibody molecule and the antigen. In one embodiment, the antigen is TAG-72. Binding specificity is typically determined from the reference point of the ability of the antibody to differentially bind the antigen of interest and an unrelated antigen, and therefore distinguish between two different antigens, particularly where the two antigens have unique epitopes. An antibody that specifically binds to a particular epitope is referred to as a "specific antibody."

A variety of methods for linking effector molecules to antibodies are well known in the art. Detectable labels useful for such purposes are also well known in the art, and include radioactive isotopes such as $^{32}P$, fluorophores, chemiluminescent agents, and enzymes. Also encompassed in the disclosure are the chemical or biochemical modifications that incorporate toxins in the antibody. In one embodiment, the toxin is chemically conjugated to the antibody. In another embodiment, a fusion protein is genetically engineered to include the antibody and the toxin. Specific, non-limiting examples of toxins are radioactive isotopes, chemotherapeutic agents, bacterial toxins, viral toxins, or venom proteins. The disclosure also includes chemical or genetically engineered modifications that link a cytokine to an antibody (such as by a covalent linkage). Specific, non-limiting examples of cytokines are interleukin (IL)-2, IL-4, IL-10, tumor necrosis factor (TNF)-alpha and interferon (IFN)-gamma.

Antigen: Any molecule that can bind specifically with an antibody. An antigen is also a substance that antagonizes or stimulates the immune system to produce antibodies. Antigens are often foreign substances such as allergens, bacteria or viruses that invade the body.

CC49 monoclonal antibody: A murine monoclonal antibody of the $IgG_1$ isotype that specifically binds TAG-72 (deposited as ATCC Accession No. HB 9459). This monoclonal antibody is a second generation monoclonal antibody prepared by immunizing mice with TAG-72 that was purified using the first generation antibody B72.3 (Colcher et al., *Proc. Natl. Acad. Sci. USA* 78:3199-3203, 1981). The CC49 monoclonal antibody efficiently targets human colon carcinoma xenografts in athymic mice and reduces or eliminates their growth (Colcher et al., *Cancer Res.* 48:4597-4603, 1988). Radiolabeled CC49 has been shown to successfully target a number of human tumors including adenocarcinoma, colorectal, breast, prostate and ovarian (Liu et al., *Cancer Biotherap Radiopharm.* 12:79-87, 1997; Macey et al., *Clin. Cancer Res.* 3:1547-1555, 1997; Meredith et al. *J. Nucl. Med.*, 37:1491-1496, 1996.)

cDNA (complementary DNA): A piece of DNA lacking internal, non-coding segments (introns) and regulatory sequences that determine transcription. cDNA is synthesized in the laboratory by reverse transcription from messenger RNA extracted from cells.

Chimeric antibody: An antibody which includes sequences derived from two different antibodies, which typically are of different species. Most typically, chimeric antibodies include human and murine antibody domains, generally human constant and murine variable regions.

Complementarity Determining Region (CDR): Amino acid sequences which together define the binding affinity and specificity of the natural Fv region of a native Ig binding site. The light and heavy chains of an Ig each have three CDRs, designated L-CDR1, L-CDR2, L-CDR3 and H-CDR1, H-CDR2, H-CDR3, respectively. By definition, the CDRs of the light chain are bounded by the residues at positions 24 and 34 (L-CDR1), 50 and 56 (L-CDR2), 89 and 97 (L-CDR3); the CDRs of the heavy chain are bounded by the residues at positions 31 and 35b (H-CDR1), 50 and 65 (H-CDR2), 95 and 102 (H-CDR3), using the numbering convention delineated by Kabat et al, (1991) *Sequences of Proteins of Immunological Interest*, 5$^{th}$ Edition, Department of Health and Human Services, Public Health Service, National Institutes of Health, Bethesda (NIH Publication No. 91-3242).

Constant Region: The portion of the antibody molecule which confers effector functions. In the present disclosure, the variant antibodies include constant regions derived from human immunoglobulins. The heavy chain constant region can be selected from any of five isotypes: alpha, delta, epsilon, gamma or mu. Heavy chains of various subclasses (such as the IgG subclass of heavy chains) are responsible for different effector functions. Thus, by choosing the desired heavy chain constant region, humanized antibodies with the desired effector function can be produced. The light chain constant region can be of the kappa or lambda type.

Cytotoxin: An agent that is toxic for cells. Examples of cytotoxins include radioactive isotopes, chemotherapeutic drugs, bacterial toxins, viral toxins, and proteins contained in venom (e.g. insect, reptile, or amphibian venom). A cytokine, such as interleukin-2 or interferon, can also be a cytotoxin.

DNA: Deoxyribonucleic acid. DNA is a long chain polymer which constitutes the genetic material of most living organisms (some viruses have genes composed of ribonucleic acid (RNA)). The repeating units in DNA polymers are four different nucleotides, each of which contains one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequence of three nucleotides in the mRNA that is transcribed from the DNA.

Effector Molecule: Therapeutic, diagnostic or detection moieties linked to an antibody, using any number of means known to those of skill in the art. Both covalent and noncovalent linkage means may be used. The procedure for linking an effector molecule to an antibody varies according to the chemical structure of the effector. Polypeptides typically contain a variety of functional groups; e.g., carboxylic acid (COOH), free amine (—$NH_2$) or sulfhydryl (—SH) groups, which are available for reaction with a suitable functional group on an antibody to result in the linkage of the effector molecule. Alternatively, the antibody is derivatized to expose or link additional reactive functional groups. The derivatization may involve linkage of any of a number of linker molecules such as those available from Pierce Chemical Company, Rockford Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

In view of the large number of methods that have been reported for linking a variety of radiodiagnostic compounds, radiotherapeutic compounds, label (e.g. enzymes or fluorescent molecules) drugs, toxins, and other agents to antibodies one skilled in the art will be able to determine a suitable method for linking a given agent to an antibody.

Encode: A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Epitope: A site on an antigen recognized by an antibody, as determined by the specificity of the antibody amino acid sequence. Epitopes are also called antigenic determinants.

Framework Region: Amino acid sequences interposed between CDRs. Includes variable light and variable heavy framework regions. The framework regions serve to hold the CDRs in an appropriate orientation for antigen binding.

High binding affinity: Affinity of an antibody for an antigen where the relative affinity of the humanized CC49 antibody is significantly greater than that of a parent CC49 antibody, for example HuCC49V10 (deposited in the American Type Culture Collection, 10801 University Boulevard, Manassas, Va. 20110-2209, on Aug. 28, 2003 as ATCC Accession No. PTA-5416). In one embodiment, affinity is calculated by a modification of the Scatchard method described by Frankel et al. (1979) *Mol. Immunol.*, 16:101-106. One of skill in the art can readily identify a statistical test that determines a statistically significant result for example, the Student's t-test, the Wilcoxon two sample test, or the Median test. In one embodiment, a high binding affinity is at least about $1.2 \times 10^{-8}$ M. In other embodiments, a high binding affinity is at least about $1.5 \times 10^{-8}$, at least about $2.0 \times 10^{-8}$, at least about $2.5 \times 10^{-8}$, at least about $3.0 \times 10^{-8}$, at least about $3.5 \times 10^{-8}$, at least about $4.0 \times 10^{-8}$, at least about $4.5 \times 10^{-8}$, or at least about $5.0 \times 10^{-8}$ M.

In another embodiment, a high binding affinity is measured by an antigen/antibody dissociation rate of a humanized CC49 antibody that is significantly lower than the parent CC49 antibody. In yet another embodiment, a high binding affinity is measured by a competition radioimmunoassay, where the amount of antibody needed for 50% inhibition of the binding of $^{125}$I-labeled HuCC49 antibody to BSM is less than that required by the parent CC49 antibody. In another embodiment, a high binding affinity is measured by flow cytometry as an increased number of gated cells labeled with humanized CC49 antibody compared to the number of cells labeled by the parent CC49 antibody.

HAMA (Human anti-murine antibody) response: An immune response in a human subject to the variable and constant regions of a murine antibody that has been administered to the patient. Repeated antibody administration may lead to an increased rate of clearance of the antibody from the patient's serum and may also elicit allergic reactions in the patient.

Humanized antibody: A human antibody genetically engineered to include mouse hypervariable regions. In one embodiment, the DNA encoding hypervariable loops of mouse monoclonal antibodies or variable regions selected in phage display libraries is inserted into the framework regions of human Ig genes. Antibodies can be "customized" to have a desired binding affinity or to be minimally immunogenic in the humans treated with them.

Humanized CC49 antibodies: CC49 antibodies humanized by grafting CC49 CDRs onto the frameworks of the relevant human antibodies (Kashmiri et al., *Hybridoma*, 14: 461-473, 1995). The murine CDRs in the resultant humanized CC49 (HuCC49) could evoke an anti-idiotypic response when administered in human subjects. CC49 can be humanized by grafting only CC49 CDRs that are important for antigen binding onto the variable light and variable heavy framework regions of, for example, LEN and 21/28'CL human antibodies (Tamura et al., *J. Immunol.* 164:1432-1441, 2000; WO 00/26394). In addition, non-specificity determining residues (SDRs) in the murine CDRs can be substituted with the corresponding residue in the human antibody. One specific, non-limiting example of a humanized CC49 monoclonal antibody is HuCC49V10 (see published PCT patent application PCT/US99/25552, herein incorporated by reference). In one embodiment, HuCC49V10 has minimal immunogenicity (compared to the parental HuCC49 antibody, at least 16-fold higher molar concentration of HuCC49V10 was required to attain 25% inhibition of HuCC49 binding to patient serum) and a partial loss in antigen-binding affinity ($1.15 \times 10^{-8}$ M) compared to the parent HuCC49 antibody ($3.20 \times 10^{-8}$ M). In one embodiment, a humanized CC49 antibody is HuCC49V10-14 (ATCC Accession Number PTA-4182, deposited in the American Type Culture Collection (10801 University Boulevard, Manassas, Va. 20110-2209) on Mar. 26, 2002, see FIG. 1; also termed HuCC49V14 in the deposit). In another embodiment, a humanized CC49 antibody is HuCC49V10-15 (ATCC Accession Number PTA-4183, deposited in the American Type Culture Collection (10801 University Boulevard, Manassas, Va. 20110-2209) on Mar. 26, 2002, see FIG. 1; also termed HuCC49V15 in the deposit).

Idiotype: the property of a group of antibodies or T cell receptors defined by their sharing a particular idiotope (an antigenic determinant on the variable region); i.e., antibodies that share a particular idiotope belong to the same idiotype. "Idiotype" may be used to describe the collection of idiotopes expressed by an Ig molecule. An "anti-idiotype" antibody may be prepared to a monoclonal antibody by methods known to those of skill in the art and may be used to prepare pharmaceutical compositions.

Immune cell: Any cell involved in a host defense mechanism. These can include, for example, T cells, B cells, natural killer cells, neutrophils, mast cells, macrophages, antigen-presenting cells, basophils, eosinophils, and neutrophils.

Immune response: A response of a cell of the immune system, such as a neutrophil, a B cell, or a T cell, to a stimulus. In one embodiment, the response is specific for a particular antigen (an "antigen-specific response"). In another embodiment, the response is against an antibody, such as HAMA response, including an anti-variable region response.

Immunoconjugate: A covalent linkage of an effector molecule to an antibody. The effector molecule can be a toxin or a detectable label. Specific, non-limiting examples of toxins include, but are not limited to, abrin, ricin, *Pseudomonas* exotoxin (such as PE35, PE37, PE38, and PE40), diphtheria toxin, anthrax toxin, botulinum toxin, or modified toxins thereof. For example, *Pseudomonas* exotoxin and diphtheria toxin are highly toxic compounds that typically bring about death through liver toxicity. *Pseudomonas* exotoxin and diphtheria toxin, however, can be modified into a form for use as an immunotoxin by removing the native targeting component of the toxin (e.g., domain Ia of *Pseudomonas* exotoxin and the B chain of diphtheria toxin) and replacing it with a different targeting moiety, such as an antibody. Other toxic agents, that directly or indirectly inhibit cell growth or kill cells, include chemotherapeutic drugs, cytokines, for example interleukin-2 or interferon, radioactive isotopes, viral toxins, or proteins contained within, for example, insect, reptile, or amphibian venom. Specific, non-limiting examples of detectable labels include, but are not limited to, radioactive isotopes, enzyme substrates, co-factors, ligands, chemiluminescent agents, fluorescent agents, haptens, or enzymes. A "chimeric molecule" is a targeting moiety, such as a ligand or an antibody, conjugated (attached or coupled) to an effector molecule. The term "conjugated" or "linked" refers to making two polypeptides into one contiguous polypeptide molecule. In one embodiment, an antibody is joined to an effector molecule. In another embodiment, an antibody joined to an effector molecule is further joined to a lipid or other molecule to a protein or peptide to increase its half-life in the antibody. The linkage can be, for example, either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule.

Immunogenicity: A measure of the ability of a targeting protein or therapeutic moiety to elicit an immune response (humoral or cellular) when administered to a subject.

Immunoreactivity: A measure of the ability of an Ig to recognize and bind to a specific antigen.

Isolated: An biological component (such as a nucleic acid, peptide or protein) that has been substantially separated, produced apart from, or purified away from other biological components in the cell of the organism in which the component naturally occurs, i.e., other chromosomal and extrachromosomal DNA and, RNA, and proteins. Nucleic acids, peptides and proteins that have been "isolated" thus include nucleic acids and proteins purified by standard purification methods. The term also embraces nucleic acids, peptides and proteins prepared by recombinant expression in a host cell as well as chemically synthesized nucleic acids.

Label: A detectable compound or composition that is conjugated directly or indirectly to another molecule to facilitate detection of that molecule. Specific, non-limiting examples of labels include fluorescent tags, chemiluminescent tags, haptens, enzymatic linkages, and radioactive isotopes.

Ligand contact residue: A residue within a CDR that is involved in contact with a ligand or antigen. A ligand contact residue is also known as a specificity determining residue (SDR). A non-ligand contact residue is a residue in a CDR that does not contact a ligand. A non-ligand contact residue can also be a framework residue.

Lymphocytes: A type of white blood cell that is involved in the immune defenses of the body. There are two main types of lymphocytes: B-cells and T-cells.

Mammal: This term includes both human and non-human mammals. Similarly, the term "subject" includes both human and veterinary subjects.

Minimally immunogenic: An antibody that generates a reduced, for example low, immune response when administered to a subject, such as a human subject. In one embodiment, immunogenicity is measured in a competitive binding assay. In one specific, non-limiting example, immunogenicity is the ability of a variant HuCC49 antibody to prevent a parental HuCC49 antibody from binding to CC49 anti-idiotypic antibodies in a patient's serum. If a variant HuCC49 antibody competes with an equal molar amount of the parental HuCC49 antibody (i.e. elicits greater than about 50% inhibition of parental HuCC49 binding to anti-idiotypic antibodies in a patient's serum) then the variant HuCC49 antibody is immunogenic. If a variant HuCC49 antibody competes poorly with an equal molar or less amount of the parental HuCC49 antibody (i.e. elicits about 50% or less inhibition of parental HuCC49 binding to anti-idiotypic antibodies in a patient's serum) then the variant HuCC49 antibody is minimally immunogenic. In another embodiment, if a five-fold or greater molar concentration of a variant HuCC49 antibody is required to achieve about 50% inhibition of binding of the parental antibody to its cognate anti-idiotypic antibodies present in a subject's sera, then the variant antibody is minimally immunogenic.

Monoclonal antibody: An antibody produced by a single clone of B-lymphocytes. Monoclonal antibodies are produced by methods known to those of skill in the art, for instance by making hybrid antibody-forming cells from a fusion of myeloma cells with immune spleen cells.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide: A linear single-stranded polynucleotide sequence of up to about 200 nucleotide bases in length, for example a polymer of deoxyribonucleotides or ribonucleotides which is at least 6 nucleotides, for example at least 15, 50, 100 or even 200 nucleotides long.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Phage display: A technique wherein DNA sequences are amplified and cloned into phage vector to create a "phage library," in which the phage present on their surface the proteins encoded by the DNA. In one embodiment, a phage library is produced that expresses HuCC49V10 variant immunoglobulins. From the rescued phages, the individual phage clones are selected through interaction of the displayed protein with a ligand, and the specific phage is amplified by infection of bacteria. Antigen specific immunoglobulins can then be expressed and characterized for their antigen binding and sera reactivity (potential immunogenicity).

Pharmaceutical agent: A chemical compound or composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell.

A "therapeutically effective amount" is a quantity of a specific substance sufficient to achieve a desired effect in a subject being treated. For instance, this can be the amount necessary to inhibit or suppress growth of a tumor or to decrease a sign or symptom of the tumor in the subject. In one embodiment, a therapeutically effective amount is the amount necessary to eliminate a tumor. When administered to a subject, a dosage will generally be used that will achieve target tissue concentrations (for example, in tumors) that has been shown to achieve a desired in vitro effect.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15$^{th}$ Edition (1975), describes compositions and formulations suitable for pharmaceutical delivery of humanized CC49 monoclonal antibodies disclosed herein.

In general, the nature of the carrier will depend on the particular mode of administration employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: A single-stranded linear nucleotide sequence, including sequences of greater than 100 nucleotide bases in length.

Polypeptide: A polymer in which the monomers are amino acid residues that are joined together through amide bonds. When the amino acids are alpha-amino acids, either the L-optical isomer or the D-optical isomer can be used, the L-isomers being preferred in nature. The term polypeptide or protein as used herein encompasses any amino acid sequence and includes, but may not be limited to, modified sequences such as glycoproteins. The term polypeptide is specifically intended to cover naturally occurring proteins, as well as those that are recombinantly or synthetically produced.

Substantially purified polypeptide as used herein refers to a polypeptide that is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

A non-conservative amino acid substitution can result from changes in: (a) the structure of the amino acid backbone in the area of the substitution; (b) the charge or hydrophobicity of the amino acid; or (c) the bulk of an amino acid side chain. Substitutions generally expected to produce the greatest changes in protein properties are those in which: (a) a hydrophilic residue is substituted for (or by) a hydrophobic residue; (b) a proline is substituted for (or by) any other residue; (c) a residue having a bulky side chain, e.g., phenylalanine, is substituted for (or by) one not having a side chain, e.g., glycine; or (d) a residue having an electropositive side chain, e.g., lysyl, arginyl, or histadyl, is substituted for (or by) an electronegative residue, e.g., glutamyl or aspartyl.

Variant amino acid sequences may, for example, be 80, 90 or even 95 or 98% identical to the native amino acid sequence. Programs and algorithms for determining percentage identity can be found at the NCBI website.

Preventing or treating a disease: Preventing a disease refers to inhibiting completely or in part the development or progression of a disease, for example in a person who is known to have a predisposition to a disease. An example of a person with a known predisposition is someone with a history of cancer in the family, or who has been exposed to factors that predispose the subject to the development of a tumor. Treating a disease refers to a therapeutic intervention that inhibits, or suppressed the growth of a tumor, eliminates a tumor, ameliorates at least one sign or symptom of a disease or pathological condition, or interferes with a pathophysiological process, after the disease or pathological condition has begun to develop.

Protein: A biological molecule encoded by a gene and comprised of amino acids.

Recombinant: A recombinant nucleic acid is one that has a sequence that is not naturally occurring or was made artificially. Artificial combination is often accomplished by chemical synthesis or, more commonly, by the artificial manipulation of isolated segments of nucleic acids, e.g., by genetic engineering techniques. Similarly, a recombinant protein is one encoded by a recombinant nucleic acid molecule.

Subject: Living multi-cellular vertebrate organisms, a category that includes both human and non-human mammals.

TAG (Tumor-Associated Glycoprotein)-72: A cell-surface glycoprotein that is expressed on human carcinomas, including adenocarcinoma, colorectal, gastric, pancreatic, breast, lung and ovarian carcinomas. TAG-72 has a high molecular weight (greater than $1 \times 10^6$) as measured by size-exclusion chromatography, a density of 1.45 g/ml, is resistant to Chondroitinase digestion, expresses blood group-related oligosaccharides, and is heavily sialylated with O-glycosidically linked oligosaccharides characteristic of mucins. These characteristics suggest that TAG-72 is a mucin-like molecule (Johnson et al., *Cancer Res.* 46:850-857, 1986, incorporated herein by reference).

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate a tumor. When administered to a subject, a dosage will generally be used that will achieve target tissue concentrations (for example, in tumors) that has been shown to achieve a desired in vitro effect.

Treatment: Refers to both prophylactic inhibition of initial infection or disease, and therapeutic interventions to alter the natural course of an untreated infection or disease process, such as a tumor growth or an infection with a bacteria.

Tumor: A neoplasm that may be either malignant or non-malignant. Tumors of the same tissue type are primary tumors originating in a particular organ (such as breast, prostate, bladder or lung). Tumors of the same tissue type may be divided into tumor of different sub-types (a classic example being bronchogenic carcinomas (lung tumors) which can be an adenocarcinoma, small cell, squamous cell, or large cell tumor). Breast cancers can be divided histologically into scirrhous, infiltrative, papillary, ductal, medullary and lobular. In one embodiment, cells in a tumor express TAG-72.

Variable region (also variable domain or V domain): The regions of both the light-chain and the heavy-chain on an Ig that contain antigen-binding sites. The regions are composed of polypeptide chains containing four relatively invariant "framework regions" (FRs) and three highly variant "hypervariable regions" (HVs). Because the HVs constitute the binding site for antigen(s) and determine specificity by forming a surface complementarity to the antigen, they are more commonly termed the "complementarity-determining regions," or CDRs, and are denoted CDR1, CDR2, and CDR3. Because both of the CDRs from the heavy- and light-chain domains contribute to the antigen-binding site, it is the three-dimensional combination of the heavy and the light chain that determines the final antigen specificity.

Within the heavy- and light-chain, the framework regions surround the CDRs. Proceeding from the N-terminus of a heavy or light chain, the order of regions is: FR1-CDR1-FR2—CDR2-FR3—CDR3-FR4. As used herein, the term "variable region" is intended to encompass a complete set of four framework regions and three complementarity-determining regions. Thus, a sequence encoding a "variable region" would provide the sequence of a complete set of four framework regions and three complementarity-determining regions.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means "including A or B, or A and B." It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Humanized CC49 Antibodies

Disclosed herein are humanized monoclonal CC49 antibodies that have a non-conservative amino acid substitution in the light chain complementarity determining region (LCDR) 3 of the CC49 antibody grafted onto a human antibody framework. In one embodiment, the humanized CC49 antibody has a non-conservative amino acid substitution of a ligand contact residue in LCDR3. In several examples, the CC49 antibody has a non-conservative substitution of a ligand contact residue at position 89, 90, 91, 92, 93, 94, 95 or 96 of LCDR3 (Table 1).

TABLE 1

| HuCC49V10 CDR sequences | | | | | | | | |
|---|---|---|---|---|---|---|---|---|
| | 89 | 90 | 91 | 92 | 93 | 94 | 95 | 96 | 97 |
| LCDR3 | Gln | Gln | Tyr | Tyr | Ser | Tyr | Pro | Leu | *Ser* |
| | 50 | 51 | 52 a | 53 | 54 | 55 | 56 | 57 |
| HCDR2 | Tyr | Phe | Ser Pro | Gly | Asn | Asp | Asp | Phe |
| | 58 | 59 | 60 | 61 | 62 | 63 | 64 | 65 |
| HCDR2 | Lys | Tyr | *Ser* | Gln | *Lys* | *Phe* | Gln | Gly |

In bold: The SDRs that are targeted for mutation.
In italic: The residues of HuCC49 already modified to generate HuCC49V10.

In one embodiment, the humanized CC49 antibody has a non-conservative amino acid substitution at position 91 of LCDR3. In one specific, non-limiting example, the humanized CC49 antibody has a tyrosine to proline substitution at position 91 of LCDR3 (see HuCC49V10-14 in FIG. 1 and in Table 2).

TABLE 2

Mutations in variants* isolated by phage display

| | LCDR1 | LCDR3 | | | | | | | |
|---|---|---|---|---|---|---|---|---|---|
| | 27b | 89 | 90 | 91 | 92 | 93 | 94 | 95 | 96 | 97 |
| HuCC49V10 | *Val* | Gln | Gln | Tyr | Tyr | Ser | Tyr | Pro | Leu | *Ser* |
| HuCC49V10-7 | Leu | — | — | — | — | Leu | — | — | — | — |
| HuCC49V10-10 | — | — | — | Ser | — | — | — | — | — | — |
| HuCC49V10-12 | — | — | — | — | — | Leu | — | — | — | — |
| HuCC49V10-13 | — | — | — | — | — | — | Thr | — | — | — |
| HuCC49V10-14 | — | — | — | Pro | — | — | — | — | — | — |
| HuCC49V10-15 | Leu | — | — | Pro | — | — | — | — | — | — |

| | HCDR2 | | | | | | | | |
|---|---|---|---|---|---|---|---|---|---|
| | 50 | 51 | 52 a | 53 | 54 | 55 | 56 | 57 |
| HuCC49V10 | Tyr | Phe | Ser Pro | Gly | Asn | Asp | Asp | Phe |
| HuCC49V10-13 | — | — | Asn — | — | — | — | — | — |
| HuCC49V10-7, -10, -12, -14, -15 | — | — | — — | — | — | — | — | — |

TABLE 2-continued

Mutations in variants* isolated by phage display

| | HCDR2 | | | | | | | |
|---|---|---|---|---|---|---|---|---|
| | 58 | 59 | 60 | 61 | 62 | 63 | 64 | 65 |
| HuCC49V10 | Lys | Tyr | *Ser* | *Gln* | Lys | Phe | *Gln* | Gly |
| HuCC49V10-13 | Gln | — | — | — | — | — | — | — |
| HuCC49V10-7, -10, -12, -14, -15 | — | — | — | — | — | — | — | — |

Bold: The SDRs targeted for mutation to generate a phage display library.
Italic: The residues of HuCC49 already modified to generate HuCC49V10.
*Variants HuCC49V10-7, -10, -12, -13, -14, and -15 can be derived from HuCC49V10 as described in Examples 1-4.

In one embodiment, the humanized CC49 antibody has no more than one non-conservative amino acid substitution in LCDR3. However, the humanized CC49 antibody can include no more than two, no more than three, no more than four, no more than five, or no more than nine non-conservative amino acid substitutions in LCDR3. In some embodiments, the CC49 antibody has a non-conservative amino acid substitution at position 91, an additional non-conservative substitution of a ligand contact residue at position 89, 90, 91, 92, 93, 94, 95 or 96 of LCDR3 (Table 1), and has a high binding affinity for TAG-72. In another embodiment, the humanized CC49 antibody has a non-conservative amino acid substitution at position 91, and has an additional non-conservative amino acid substitution of a non-ligand contact residue of LCDR3.

A humanized CC49 monoclonal antibody including a non-conservative amino acid substitution in LCDR3 can also include an additional non-conservative amino acid substitution in a region other than LCDR3. For example, an additional non-conservative amino acid substitution can be a non-conservative substitution in another LCDR or in an HCDR. Specific, non-limiting examples of a humanized CC49 monoclonal antibody that includes more than one non-conservative substitution are a humanized CC49 monoclonal antibody with a non-conservative substitution in an LCDR3 ligand contact residue and a non-conservative substitution in an LCDR non-ligand contact residue, or a non-conservative substitution in LCDR3 and a non-conservative substitution in HCDR2. In several embodiments, the CC49 antibody has a non-conservative substitution of a ligand contact residue at position 50, 51, 52, 52a, 53, 54, 56, 57, or 58 of HCDR2 (Table 1) in addition to an LCDR3 non-conservative substitution. In another embodiment, the humanized CC49 antibody has an additional non-conservative amino acid substitution in a framework residue.

In one embodiment, the humanized CC49 antibody has a conservative amino acid substitution in addition to an LCDR3 non-conservative substitution, such as, but not limited to, a conservative substitution in a CDR in addition to an LCDR3 non-conservative substitution. In other specific non-limiting examples, the humanized CC49 antibody has a conservative substitution in an LCDR or in an HCDR in addition to an LCDR3 non-conservative substitution. In other specific non-limiting examples, the humanized CC49 antibody has a conservative substitution in LCDR1, LCDR2, LCDR3, HCDR1, HCDR2, or HCDR3 in addition to an LCDR3 non-conservative substitution. Thus in another specific, non-limiting example, the humanized CC49 antibody has a conservative amino acid substitution at position 27b of LCDR1 and a non-conservative amino acid substitution at position 91 of LCDR3. A specific, non-limiting example of a conservative amino acid substitution is a valine to leucine substitution at position 27b of LCDR1 and specific, non-limiting example of a non-conservative amino acid substitution is a tyrosine to proline substitution at position 91 of LCDR3 (see HuCC49V10-15 in FIG. 1 and in Table 2).

In one embodiment, the humanized CC49 antibody has a CH2 domain deletion. In one specific embodiment, a humanized CC49 antibody with a CH2 domain deletion is cleared more quickly from the plasma compared to the parent CC49 antibody. In another specific embodiment, a humanized CC49 antibody with a CH2 domain deletion has reduced immunogenicity compared to the parent CC49 antibody.

The humanized monoclonal antibodies disclosed herein bind TAG-72 with high binding affinity. In one embodiment, the humanized CC49 antibody has a high binding affinity for TAG-72 that is at least about $1.2 \times 10^{-8}$ M. In other embodiments, the humanized CC49 antibody has a high binding affinity for TAG-72 that is at least about 1.2, $10^{-8}$, about $1.5 \times 10^{-8}$, about $2.0 \times 10^{-8}$, about $2.5 \times 10^{-8}$, about $3.0 \times 10^{-8}$, about $3.5 \times 10^{-8}$, about $4.0 \times 10^{-8}$, about $4.5 \times 10^{-8}$, or about $5.0 \times 10^{-8}$ M. In one embodiment, the humanized CC49 antibody has a high binding affinity if it has a significantly lower antigen/antibody dissociation rate compared to that of the parent CC49 antibody. In another embodiment, the humanized CC49 antibody has a high binding affinity if less antibody is required for a 50% inhibition of the binding of $^{125}$I-labeled-HuCC49 to BSM compared to the parent CC49 antibody. In yet another embodiment, the humanized CC49 antibody has a high binding affinity when the number of cells labeled with humanized CC49 antibody is significantly greater than the number of cells labeled by the parent CC49 antibody, as measured by flow cytometry.

Immunogenicity of variant HuCC49 antibodies can be measured in a competitive binding assay as the ability of a variant HuCC49 antibody to prevent a parent CC49 or HuCC49 antibody from binding to anti-idiotypic antibodies in a human subject's serum. In one embodiment, a variant humanized CC49 antibody with a non-conservative amino acid substitution in LCDR3 is minimally immunogenic in a subject. In other embodiments, the variant humanized CC49 antibody with an additional amino acid substitution is minimally immunogenic. In one embodiment, at least about five-fold higher molar concentration of the variant humanized CC49 antibody, than that of the parental HuCC49 antibody, is required to elicit 50% inhibition of the parental HuCC49 binding to its cognate anti-idiotypic antibodies in a subject's sera. In other embodiments, at least about ten-fold, at least about twenty five-fold, at least about fifty-fold, at least about seventy-fold, or at least about one hundred-fold higher molar concentration of the variant humanized CC49 antibody, than that of the parental antibody, is required to elicit 50% inhibition of the parental HuCC49 binding to its cognate anti-idiotypic antibodies in a subject's sera.

Effector molecules, e.g., therapeutic, diagnostic, or detection moieties, can be linked to a humanized CC49 antibody that specifically binds TAG-72, using any number of means known to those of skill in the art. Thus, a humanized CC49 antibody with a non-conservative amino acid substitution can have any one of a number of different types of effector molecules linked to it. In one embodiment, the humanized CC49 antibody is linked to a detectable label. In some embodiments, the humanized CC49 antibody is linked to a radioactive isotope, an enzyme substrate, a co-factor, a ligand, a chemiluminescent agent, a fluorescent agent, a hapten, or an enzyme. In another embodiment, the humanized CC49 antibody is linked to a cytotoxin. In other embodiments, the humanized CC49 antibody is linked to a chemotherapeutic drug, a radioactive isotope, a bacterially-expressed toxin, a virally-expressed toxin, or a venom protein. In yet other embodiments, the humanized CC49 antibody is linked to a cytokine. Specific, non-limiting examples of cytokines are IL-2, IL-4, IL-10, TNF-alpha and IFN-gamma. In some embodiments, the humanized CC49 antibody is linked to an effector molecule by a covalent or non-covalent means.

Pharmaceutical Compositions and Therapeutic Methods

Pharmaceutical compositions are disclosed herein that include a humanized CC49 monoclonal antibody, such as HuCC49V10-14 or HuCC49V10-15, and can be formulated with an appropriate solid or liquid carrier, depending upon the particular mode of administration chosen. In addition, a humanized CC49 monoclonal antibody linked to an effector molecule (i.e., toxin, chemotherapeutic drug, or detectable label) can be prepared in pharmaceutical compositions.

The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the pharmaceutical composition to be administered can also contain minor amounts of non-toxic auxiliary substances, such as wetting or emulsifying agents, preservatives, and pH buffering agents and the like, for example sodium acetate or sorbitan monolaurate.

The dosage form of the pharmaceutical composition will be determined by the mode of administration chosen. For instance, in addition to injectable fluids, topical, inhalation, oral and suppository formulations can be employed. Topical preparations can include eye drops, ointments, sprays and the like. Inhalation preparations can be liquid (e.g., solutions or suspensions) and include mists, sprays and the like. Oral formulations can be liquid (e.g., syrups, solutions or suspensions), or solid (e.g., powders, pills, tablets, or capsules). Suppository preparations can also be solid, gel, or in a suspension form. For solid compositions, conventional non-toxic solid carriers can include pharmaceutical grades of mannitol, lactose, starch, or magnesium stearate. Actual methods of preparing such dosage forms are known, or will be apparent, to those skilled in the art.

The pharmaceutical compositions that include a humanized CC49 monoclonal antibody can be formulated in unit dosage form suitable for individual administration of precise dosages. In addition, the pharmaceutical compositions may be administered as an immunoprophylactic in a single dose schedule or as an immunotherapy in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgement of the administering practitioner. In one specific, non-limiting example, a unit dosage can be about 0.1 to about 10 mg per patient per day. Dosages from about 0.1 up to about 100 mg per patient per day may be used, particularly if the agent is administered to a secluded site and not into the circulatory or lymph system, such as into a body cavity, into a lumen of an organ, or directly into a tumor. In one embodiment, about 10 mCi of a radiolabeled humanized CC49 monoclonal antibody is administered to a subject. In other embodiments, about 15 mCi, about 20 mCi, about 50 mCi, about 75 mCi or about 100 mCi of a radiolabeled humanized CC49 monoclonal antibody is administered to a subject. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The compounds of this disclosure can be administered to humans on whose tissues they are effective in various manners such as topically, orally, intravenously, intramuscularly, intraperitoneally, intranasally, intradermally, intrathecally, subcutaneously, via inhalation or via suppository. The particular mode of administration and the dosage regimen will be selected by the attending clinician, taking into account the particulars of the case (e.g. the subject, the disease, the disease state involved, and whether the treatment is prophylactic).

In one embodiment, a therapeutically effective amount of a humanized CC49 antibody, such as HuCC49V10-14 or HuCC49V10-15, is the amount of humanized CC49 antibody necessary to inhibit further growth of a TAG-72-expressing tumor or suppress the growth of a TAG-72-expressing tumor, without eliciting a HAMA response in the patient receiving the treatment. In other embodiments, a therapeutically effective amount of humanized CC49 antibody is the amount of humanized CC49 antibody necessary to eliminate or reduce the size of a TAG-72-expressing tumor, without eliciting a HAMA response. Specific, non-limiting examples of TAG-72-expressing tumors are adenocarcinoma, colorectal, gastric, pancreatic, breast, lung, and ovarian tumors. In yet another embodiment, a therapeutically effective amount of humanized CC49 antibody is an amount of humanized CC49 antibody that is effective at reducing a sign or a symptom of the tumor and induces a minimal immune response.

A therapeutically effective amount of a humanized CC49 monoclonal antibody, such as HuCC49V10-14 or HuCC49V10-15, can be administered in a single dose, or in several doses, for example daily, during a course of treatment. In one embodiment, treatment continues until a therapeutic result is achieved. However, the effective amount of humanized CC49 antibody will be dependent on the subject being treated, the severity and type of the affliction, and the manner of administration of the therapeutic(s).

Controlled release parenteral formulations of a humanized CC49 monoclonal antibody can be made as implants, oily injections, or as particulate systems. For a broad overview of protein delivery systems (see Banga, A. J., Therapeutic Peptides and Proteins: Formulation, Processing, and Delivery Systems, Technomic Publishing Company, Inc., Lancaster, Pa., 1995). Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly (see Kreuter, J., Colloidal Drug Delivery Systems, J. Kreuter, ed., Marcel Dekker, Inc., New York, N.Y., pp. 219-342, 1994; Tice & Tabibi, Treatise on Controlled Drug Delivery, A. Kydonieus, ed., Marcel Dekker, Inc. New York, N.Y., pp. 315-339, 1992).

Polymers can be used for ion-controlled release. Various degradable and nondegradable polymeric matrices for use in controlled drug delivery are known in the art (Langer, R., *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec et al., *J. Parent. Sci. Tech.* 44:58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri, et al., Liposome Drug Delivery Systems, Technomic Publishing Co., Inc., Lancaster, Pa., 1993). Numerous additional systems for controlled delivery of therapeutic proteins are known (e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496).

Site-specific administration of the disclosed compounds can be used, for instance by applying the humanized CC49 antibody to a pre-cancerous region, a region of tissue from which a tumor has been removed, or a region suspected of being prone to tumor development. In some embodiments, sustained intra-tumoral (or near-tumoral) release of the pharmaceutical preparation that includes a therapeutically effective amount of the humanized CC49 antibody may be beneficial.

The present disclosure also includes therapeutic uses of humanized CC49 monoclonal antibodies that are non-covalently or covalently linked to effector molecules. In one specific embodiment, the humanized CC49 monoclonal antibody is covalently linked to an effector molecule that is toxic to a tumor or cell expressing TAG-72. In one specific, non-limiting example, the effector molecule is a cytotoxin. In other specific, non-limiting examples the effector molecule is a radioactive isotope, a chemotherapeutic drug, a bacterially-expressed toxin, a virally-expressed toxin, a venom protein, or a cytokine. Humanized CC49 monoclonal antibodies covalently linked to an effector molecule have a variety of uses. For example, a humanized CC49 antibody linked to a radioactive isotope us if use in immunotherapy. A humanized CC49 antibody covalently linked to a radioactive isotope is of use to localize a tumor in radioimmunoguided surgery, such that the tumor can be removed.

The present disclosure also includes combinations of a humanized CC49 monoclonal antibody, such as HuCC49V10-14 or HuCC49V10-15, with one or more other agents useful in the treatment of tumors. For example, the compounds of this disclosure can be administered in combination with effective doses of immunostimulants, anti-cancer agents, anti-inflammatory agents, anti-infectives, and/or vaccines. The term "administration in combination" or "co-administration" refers to both concurrent and sequential administration of the active agents. A subject that is suffering from a tumor, or is predisposed to the development of a tumor, will be a candidate for treatment using the therapeutic methods disclosed herein.

Diagnostic Methods and Kits

A method is provided herein for the in vivo or in vitro detection of TAG-72-expressing tumors or cells. An in vivo detection method can localize any tumor or cell that expresses TAG-72 in a subject. In one embodiment, a humanized CC49 antibody is administered to the subject for a sufficient amount of time for the antibody to localize to the tumor or cell in the subject and to form an immune complex with TAG-72. The immune complex can then be detected. In one specific, non-limiting example detection of an immune complex is performed by immunoscintography. Other specific, non-limiting examples of immune complex detection include radiolocalization, radioimaging, or fluorescence imaging. In another embodiment, the antibody is linked to an effector molecule. In one specific, non-limiting embodiment, the effector molecule is a detectable label. Specific, non-limiting examples of detectable labels include a radioactive isotope, an enzyme substrate, a co-factor, a ligand, a chemiluminescent agent, a fluorescent agent, a hapten, or an enzyme.

A method of detecting tumors in a subject includes the administration of a humanized CC49 antibody complexed to an effector molecule, such as a radioactive isotope. In one embodiment, a humanized CC49 antibody complexed to an effector molecule, such as a radioactive isotope, is administered to a subject prior to surgery or treatment. In another embodiment, a humanized CC49 antibody complexed to an effector molecule, such as a radioactive isotope, is administered to a subject following surgery or treatment. After a sufficient amount of time has elapsed to allow for the administered radiolabeled antibody to localize to the tumor, the tumor is detected. In one specific embodiment, the detection step is performed prior to surgery. In another embodiment, the detection step is performed during surgery, for example to detect the location of the tumor prior to removing it, as in radioimmunoguided surgery. In yet another embodiment, the detection step is performed after surgery to ensure the complete removal of the tumor, or to detect a recurrence of the tumor. In one specific, non-limiting example, a radiolabeled immune complex is detected using a hand held gamma detection probe. Primary tumors, metastasized tumors or cells expressing TAG-72 can be detected.

In another embodiment, a humanized CC49 antibody and a secondary antibody are administered to the subject for a sufficient amount of time for the humanized CC49 antibody to form an immune complex with TAG-72 on a tumor or cell, and for the secondary antibody to form an immune complex with the humanized CC49 antibody. In one embodiment, the humanized CC49 antibody is complexed with the secondary antibody prior to their administration to the subject. In one specific, non-limiting embodiment, the secondary antibody is linked to a detectable label. In one embodiment, the immune complex, which includes TAG-72, the humanized CC49 antibody, and the secondary antibody linked to a detectable label, is detected as described above.

An in vitro detection method can screen any biological sample containing any tumor or cell that expresses TAG-72. Such samples include, but are not limited to, tissue from biopsies, autopsies, and pathology specimens. Biological samples also include sections of tissues, such as frozen sections taken for histological purposes. Biological samples further include body fluids, such as blood, serum, saliva, or urine. A biological sample is typically obtained from a mammal, such as a human. In one embodiment the subject has a colorectal tumor. In other embodiments, the subject has a gastric tumor, a pancreatic tumor, a breast tumor, a lung tumor, an adenocarcinoma, or an ovarian tumor. Other biological samples that can be detected by the in vitro detection method include samples of cultured cells that express TAG-72.

In one embodiment, a method is provided for detecting a TAG-72-expressing tumor or cell. Kits for detecting a TAG-72-expressing tumor or cell will typically comprise a humanized CC49 antibody that specifically binds TAG-72. In some embodiments, an antibody fragment, such as an Fv fragment is included in the kit. In a further embodiment the antibody is an immunoconjugate. In some embodiments, the antibody is conjugated to a detectable label (e.g. radioactive isotope, enzyme substrate, co-factor, ligand, fluorescent agent, hapten, enzyme, or chemiluminescent agent).

The kit can include instructional materials disclosing means of use of an antibody that specifically binds TAG-72 or fragment thereof (e.g. for detection of TAG-72-expressing cells in a sample). The instructional materials may be written, in an electronic form (e.g. computer diskette or compact disk) or may be visual (e.g. video files). The kits may also include additional components to facilitate the particular application for which the kit is designed. Thus, for example, the kit may additionally contain means of detecting a label (e.g. enzyme substrates for enzymatic labels, filter sets to detect fluorescent labels, appropriate secondary labels such as a secondary antibody, or the like). In one embodiment, the kit contains a secondary antibody that is conjugated to a detectable label. The kits may additionally include buffers and other reagents, such as an antigen (e.g. purified TAG-72) routinely used for the practice of a particular method. Such kits and appropriate contents are well known to those of skill in the art.

In one embodiment of the present invention, the diagnostic kit comprises an immunoassay. Although the details of the immunoassays may vary with the particular format employed, the method of detecting TAG-72 or fragment thereof in a biological sample generally includes the steps of contacting the biological sample with an antibody which specifically reacts, under immunologically reactive conditions, to TAG-72. The antibody is allowed to specifically bind under immunologically reactive conditions to form an immune complex, and the presence of the immune complex (bound antibody) is detected directly or indirectly.

The invention is illustrated by the following non-limiting Examples.

EXAMPLES

Example 1

Construction of the Variant HuCC49V10 Antibody Phage Library

A phage display library of isolates was derived from the humanized CC49 variant HuCC49V10 (Tamura et al., *J. Immunol.*, 164: 1432, 2000) by the mutagenesis of the LCDR3 and the HCDR2, the two CDRs that were earlier shown to be the targets of the patient's anti-variable region response. Primer-induced mutagenesis was used to replace the targeted SDRs of the two CDRs (Table 1) with all possible residues located at the corresponding positions in human antibodies (Table 3). A dual step PCR (Landt et al., *Gene* 96: 125, 1990) was used for DNA amplification.

TABLE 3

| Residue substitutions in the library | |
|---|---|
| | Encoded aa |
| L-CDR3 | |
| Position 89: | R,L,N,K,M,H,Q,I,S |
| Position 91: | S,Y,R,A,G,H,T,C,P,D,N |
| Positions 92, 93, 94, 96: | S,R,L,V,A,G,T,P,Y,F,D,N, I,W,H,E,L,Q,M,C |
| H-CDR2 | |
| Positions 50, 52, 53, 58: | S,R,L,V,A,G,T,P,Y,F,D,N, I,W,H,E,L,Q,M,C |
| Position 54: | S,T,D,G,F,N,R,L,I,A,V,Y, C,H,P |
| Position 56: | S,T,A,G,V,L,R,I,D,E,Y,C, W,F,L,N,M, |

DNA Amplification

For the first step of DNA amplification, a primer derived from the leader sequence of the light (SEQ ID NO: 1) or heavy (SEQ ID NO: 9) chain was used as the 5' primer, while the degenerate mutagenic primers for each of the light (SEQ ID NO: 2-7) or heavy (SEQ ID NO: 10-15) chain were mixed together and used as 3' primers (see Table 4 for primer sequences of SEQ ID NO: 1-12). The degenerate primers were mixed in a ratio that made all the 3' primers equimolar in concentration. For the second step of the amplification, the gel purified product of the first round of PCR served as the 5' primer, while the 3' primer was derived from the 3'-end of the light chain (SEQ ID NO: 8) or the 3'-end of the CH1 region of the heavy chain (SEQ ID NO: 16).

TABLE 4

Oligonucleotide primers used to generate the library of genes encoding light chains and Fd regions of the variants of HuCC49V10

| Name | Sequence | SEQ ID NO. |
|---|---|---|
| 5' V$_L$ | 5'-TGAGCGGCACA*GAGCTC*GACATCGTGATGAG-3' | 1 |
| 3' 89 V$_L$ | 5'-AGCTATAATACTGSHKACAATAATAG-3' | 2 |
| 3' 91 V$_L$ | 5'-GGGGATAGCTATAGBNCTGCTGACAA-3' | 3 |
| 3' 92 V$_L$ | 5'-TGAGGGGATAGCTSNNATACTGCTGA-3' | 4 |
| 3' 93 V$_L$ | 5'-AGCTGAGGGGATASNNATAATACTGC-3' | 5 |
| 3' 94 V$_L$ | 5'-CGAAGCTGAGGGGSNNGCTATAATAC-3' | 6 |
| 3' 96 V$_L$ | 5'-CAGCGCCGAAGCTSNNGGGATAGCTA-3' | 7 |
| 3' V$_L$ | 5'-GCGCCGTC*TAGA*ATTAACACTCTCCCCTGTTGAAGCTCTTTGTGACGGGCGAACTCAG-3' | 8 |
| 5' V$_H$ | 5'-GCCCGTA*CCATGG*CCCAGGTCCAGCTGGTGCA-3' | 9 |
| 3' 50 V$_H$ | 5'-CGGGGAGAGAASNNTCCAATCCACT-3' | 10 |
| 3' 52 V$_H$ | 5'-CGTTTCCGGGSNNGAAATATCCAA-3' | 11 |
| 3' 53 V$_H$ | 5'-AATCATCGTTSNNGGGAGAGAAAT-3' | 12 |
| 3' 54 V$_H$ | 5'-AAAAATCATCGNNTCCGGGAGAGA-3' | 13 |
| 3' 56 V$_H$ | 5'-AGTACTTAAASNHATCGTTTCCGG-3' | 14 |
| 3' 58 V$_H$ | 5'-TCTGTGAGTASNNAAAATCATCGT-3' | 15 |
| 3' V$_H$ | 5'-GCATGTA*CTAGT*TTTGCACAAGATTTGG-3' | 16 |

S = G/C
H = A/C/T
K = G/T
B = G/T/C
N = A/G/C/T

The oligonucleotide primers used for DNA amplification, listed in Table 4, were supplied by Biosynthesis Inc. (Lewisville, Tex.). They were purified by polyacrylamide gel electrophoresis. Each of the 5' primers used for the first step PCR and the 3' primers used for the second step PCR carry a unique restriction endonuclease site at its flank. The 5' VL (SEQ ID NO: 1) carried a Sac I site, while the 3' VL (SEQ ID NO: 8) had Xba I site. The 5' VH (SEQ ID NO: 9) and the 3' VH primers carried Nco I and Spe I sites, respectively. To eliminate an existing Sac I site from the constant region of the kappa chain, a point mutated Sac I site was incorporated into the 3' VL primer.

The first PCR was carried out in a final volume of 50 μl containing 10 ng of template, 200 μM dNTPs and 5 units of Taq polymerase (Gibco BRL, Gaithersburg, Md.). The PCR mix contained 200 pmol of each of the 5' and 3' primers; the latter being a mixture of degenerate primers. Thirty cycles of a denaturing step at 94° C. for 30 seconds, a primer annealing step at 55° C. for 50 seconds, and a polymerization step at 72° C. for 60 seconds were followed by a final primer extension step for 10 minutes at 72° C. The second PCR consisted of 30 cycles of denaturation (94° C. for 30 seconds), primer annealing (55° C. for 90 seconds) and polymerization (72° C. for 90 seconds) followed by a final extension for 10 minutes at 72° C.

Phagemid Vector

A phagemid vector pComb3H-SS (Barbas, C. F. and Burton, D. R. Cold Spring Harbor Laboratory Course on Monoclonal Antibodies From Combinatorial Libraries, Cold Spring Harbor, N.Y., 1994) was used to generate a combinatorial library of the mutated HuCC49V10 Fabs displayed on the surface of the filamentous phage M13. The SS designation is used for pComb3H vector when it carries a 1200 bp stuffer sequence in place of Ig light chain (SS I), and a 300 bp sequence as a stuffer in place of Ig heavy chain (SS II). PComb3H-SS, a modified version of the original pComb3 vector (Barbas et al., *Proc. Natl. Acad. Sci. USA* 88: 7978, 1991), was obtained from Dr. Carlos Barbas of Scripps Research Institute, LaJolla, Calif.

pComb3 contains both the origin of replication of the plasmid ColE1 and origin of replication of the filamentous bacteriophage f1. The plasmid contains the gene for ampicillin (carbenicillin) resistance. More importantly, it is designed to carry a number of unique and convenient restriction endonuclease sites (FIG. 2). The restriction fragment EcoR I/Sac I located downstream from lac Z promoter carries a ribosomal binding site and the outer membrane (ompA) leader sequence of *E. coli*. A sequence encoding an Ig light chain can be inserted as a Sac I/Xba I fragment, immediately downstream from the omp A. Located 3' to omp A is a Xba I/Nco I fragment that contains a stop codon for the translation of the light chain, a ribosomal binding site for the translation of the second protein from the bicistronic message, and a pel B leader peptide of *E. carotovora*. A sequence encoding the Fd fragment can be inserted as a Nco I/Spe I fragment, immediately downstream from the pel B leader. This is followed by a Spe I/Not I fragment that contains the carboxy-terminal part of the gene III protein of phage M13 and two tandem stop codons. The carboxy-terminal part of gene III, which is fused to the Fd through a flexible linker, is located on a Spe I/Nhe I fragment. This fragment can be removed by cleavage with Spe I/Nhe I, followed by re-ligation which is possible because cleavage with the two enzymes generates identical cohesive ends. The leader peptides facilitate transport of the expressed light chain and Fd fragments to the periplasm, where the leader peptides are proteolytically cleaved and the free light chains and Fd fragments assemble into Fabs. The carboxyl-terminal half of gene III serves a capping role in the morphogenesis of filamentous phages. In the presence of the helper phage, one Fab-gene III fusion protein molecule along with 3-4 molecules of the native gene III protein are displayed on the phage surface. The helper phage is essential for replication and assembly of phage particles, because pComb3 is devoid of all these genes. The helper phage, VCSM13, used here for the rescue of the phage particles carries a kanamycin resistance gene that facilitates selection of bacteria infected with the helper virus. A recombination-deficient strain of *E. coli*, XL1-Blue, carrying a transposon 10 in its F' factor has been used to develop the phage display libraries. The F' factor is essential for the susceptibility of bacteria to the male-specific phages. Transposon 10 carries a tetracycline resistance gene.

Library Construction

To clone the light chain PCR products in pComb3H vector, the PComb3H-SS plasmid was simultaneously treated with 5 units of Sac I and 9 units of Xba I for each microgram of DNA in a reaction mixture of appropriate volume containing the desired buffer. The reaction mixture was incubated for 3 hours at 37° C. The DNA was ethanol precipitated, pelleted, washed with 70% ethanol, air dried and suspended in 100 μl of Tris-EDTA (TE) buffer (pH 8.0). To isolate the linearized vector, the DNA was electrophoresed through 0.6% agarose gel. The gel containing a band of approximately 3.7 Kb DNA, visualized by ethidium bromide staining, was excised and the DNA was recovered from the agarose slice by electroelution. The recovered DNA was ethanol precipitated, pelleted, washed, dried and resuspended in TE buffer as before. Similarly, the PCR products generated by using the light chain primers were treated with Sac I/Xba I, and the purified Sac I/Xba I fragments were electrophoresed through a 2% agarose gel. The 750 bp DNA band was excised, and the DNA fragments were recovered from the gel by electroelution, as described earlier. Multiple reactions were set up to ligate the Sac I/Xba I linearized vector and the Sac I/Xba I digested PCR products. Ligation was performed for 1 hour at room temperature, using a commercially available ligation kit (Gibco BRL, Gaithersberg, Md.). The ligation reactions were pooled and the DNA was ethanol precipitated, pelleted, washed, dried and resuspended in 15 µl of water. Electroporation-competent XL-1Blue cells (Stratagene, La Jolla, Calif.) were transformed with the ligated DNA by electroporation. Using an electroporator (BioRad, Hercules, Calif.), a pulse of 1700 volts at the field strength of 17 kV/cm was applied for 5 milliseconds. A series of transformations were performed and pooled together. After adding SOC medium (Gibco BRL), the transformation mix was incubated at 37° C. for 1 hour. Subsequently, Super Broth (Gibco BRL) containing 50 µg/ml of carbenicillin and 10 µg/ml of tetracyclin was added and the culture was incubated at 37° C. on a shaker, overnight. The plasmid was isolated from the transformed cells, using a maxiprep kit (Qiagen, Valencia, Calif.). The isolated plasmid was linearized by digestion with 3 units of Spe I and 9 units of of Nco I per µg of the DNA. A procedure similar to that described for preparing Sac I/Xba I linearized vector was used to prepare Nco I/Spe I linearized plasmid. Similarly, the PCR products that were generated by using the heavy chain primers were digested with Nco I/Spe I and purified. The purified PCR products were inserted into the vector by ligation, and the ligation mixture was used to transform XL-1 Blue cells, by electroporation. After adding tetracyclin- and carbenicillin-supplemented Super Broth to the culture and incubating for 1 hour at 37° C., 1 ml of VCSM13 helper phage (Stratagene) containing approximately $10^{12}$ pfus (plaque forming units) was added to the culture. After incubation for 2 hour, kanamycin (70 µg/ml) was added and the culture was shaken overnight at 37° C. Next morning, cells were spun down (4,000 rpm, 15 minutes, 4° C.) and the phage was precipitated from the supernatant by adding PEG-8000and NaCl to the final concentration of 4% and 3%, respectively, and incubating on ice for 30 minutes. The precipitate was collected by centrifugation (9,000 rpm, 20 minutes, 4° C.). The pellet was suspended in 2 ml of Tris borate saline (TBS) containing 1% BSA. The phage was titered by infecting XL-1Blue cells ($OD_{600}$=0.5) with serial dilutions of phage suspension, and plating the infected cells on LB/carbenicillin plates.

Example 2

Selection of TAG-72-Binding HuCC49V10 Variants and Production of Soluble Fabs

The phage library was screened and enriched for isolates binding to TAG-72. To that end, the library was subjected to multiple (7) rounds of panning. During each round, variants that specifically bind to TAG-72 were selected and amplified. The selected variants were used as a source of phagemids that were isolated and genetically manipulated en mass to express soluble Fab molecules.

Panning

For panning, a modification of the procedure that has been described earlier (Parmley and Smith *Gene* 73:305, 1988; Barbas et al., *Proc. Natl. Acad. Sci. USA* 88: 7978, 1991) was used. During each round of panning, variants that specifically bind to TAG-72 were selected and amplified. ELISA plates (Nalgene Nunc International, Rochester, N.Y.) were coated overnight at 4° C. with 50 µl of TAG-72 positive bovine submaxillary mucin (BSM) (Type 1-S; Sigma, St Louis, Mo.) in D-PBS with calcium and magnesium chloride (Gibco BRL). The amount of BSM was progressively reduced from 1.0 µg to 0.01 µg/well, with increasing rounds of panning. The wells were washed with water and blocked by incubating with milk blocking solution (KPL, Gaithersburg, Md.) at 37° C. for 1 hour. Fifty µl of phage (0.15-5×$10^{12}$ pfus) suspended in 50 µl of milk diluent solution (KPL) was pre-incubated at room temperature for 30 minutes, before it was added to the wells and incubated at 4° C. overnight. After removing the milk/phage solution, the wells were washed by pipetting TBS/0.5% Tween 20 vigorously up and down. The washing cycles were progressively increased with increasing rounds of panning. Finally the phage was eluted by adding 50 µl of elution buffer (0.1 M HCl, pH 2.2/BSA 1 mg/ml) and incubating for 10 minutes at room temperature. The eluate was removed and neutralized with 43 µl of 1 M Tris base. The eluted phage was used to infect growing XL-1 Blue cells, at room temperature for 15 minutes, and the virus was replicated in the presence of helper phage VCSM13. Super Broth (SB) medium containing carbenicillin and tetracycline was added, and the culture was shaken at 37° C. for 1 hour. Phage preparations and pannings were repeated, as described earlier. After the final round of panning, the virus was harvested, precipitated and re-suspended in TBS/1% BSA.

The stringent condition of panning (decreasing amounts of BSM on the plate and increasing number of washing cycles with the higher rounds of panning) reduced the titer of the eluted phage from 1.2×$10^9$ in the first round to 1.3×$10^6$ in the seventh round. The phage eluted from the seventh round was amplified to a titer of approximately 2×$10^{13}$. Thus, a significant enrichment of TAG-72 binding variants was achieved.

Preparation of Soluble Fab: Genetic Manipulation of Phagemid for Soluble Fab Expression The phage eluted from the last round of panning was used to infect logarithmically growing XL-1Blue cells. The culture was grown in SB medium containing carbenicillin (20 µg/ml) and tetracycline (10 µg/ml), overnight at 37° C. Cells were collected by pelleting and phagemid DNA was isolated. The DNA was digested by treatment with Nhe I/Spe I to remove DNA fragment that encodes gene III. The enzyme treated DNA was electrophoresed on a 0.6% agarose gel. The large DNA fragment was gel purified, self-ligated and used to transform competent XL-1Blue cells. Transformation mixture was streaked on LB/carbenicillin plates. After incubating the plates o/n at 37° C., fifty individual colonies were inoculated in 10 ml of SB medium containing 20 mM $MgCl_2$ and 50 µg/ml carbenicillin. Cultures were grown at 37° C. for 6 hours, before isopropyl-β-D thiogalactopyranoside (IPTG) was added to a final concentration of 1 mM for the induction of the Fab expression. The culture was then shifted to 30° C. and shaken overnight. Cells were recovered by centrifugation. A part of the cell pellet was saved to isolate the phagemid for the subsequent sequence analysis of the variants. The rest of the cell pellet was resuspended in 1 ml of PBS and lysed by four cycles of freezing in a dry ice-ethanol bath for 5 minutes and thawing in a 37° C. water bath. The cell debris was pelleted by centrifugation at 15,000 rpm, and the supernatant was collected for the Fab assay.

Example 3

Screening for High-Binding-Affinity Variants of HuCC49V10

Cell lysates from all 48 cultures of the XL-1Blue cells transformed by the Fab constructs of pComb3H lacking the gene III fragment were tested for the presence of Fab by ELISA and Western Blot analysis. The cell lysates that were found positive were then screened for binding to the TAG-72 positive BSM by Surface Plasmon Resonance (SPR).

ELISA

Supernatants from each of the 48 cell lysates were screened to detect Fab by ELISA assay that has earlier been described (Tamura et al., *J. Immunol.* 164:1432, 2000; Bei et al., *J. Immunol. Methods* 186: 245, 1995). Individual wells of the 96-well polyvinyl microtiter plates were coated with 0.1 µg (50 µl) of goat anti-human kappa (Southern Biotechnology Associate, Inc., Bringham, Ala.). The plates were blocked with 5% BSA in PBS for 1 hour at 37° C. and then washed with 1% BSA in PBS. Fifty µl of the supernatant to be tested was loaded in each well. After a 1 hour incubation at 37° C., plates were washed with 1% BSA in PBS. This was followed by adding 100 µl of 1:5,000 dilution (in 1% BSA in PBS) of peroxidase-conjugated goat anti-human IgG (Fab)$_2$ fragment specific antibody (Jackson Immuno Research Lab, West Grove, Pa.). The plates were incubated for another hour at 37° C. They were washed prior to the addition of 100 µl of freshly prepared substrate ($H_2O_2$) mixed with o-phenylene diamine hydrochloride as a chromogen (Sigma, St. Louis, Mo.). The colorimetric reaction was allowed to proceed for 10 min at room temperature in the dark, before it was terminated by the addition of 50 µl of 4N $H_2SO_4$ per well. The absorbance was read at 490 nm.

Of the 48 lysates that were tested in duplicate, a great majority of them were positive, and many among them were strongly positive for the Fab.

Western Blot Analysis

The presence of soluble Fab in cell lysates was also tested by Western Blot Forty µl of the supernatant from each of the 48 cell lysates was electrophoresed on a 4-20% pre-cast SDS-polyacrylamide gel. Two sets of SDS-PAGE were carried out, one under reducing and the other under non-reducing conditions. The proteins were electro-blotted on to the Immobilon-P membrane (Millipore, Bedford, Mass.) according to the instructions of the manufacturer. The blotted membrane was saturated with 5% milk for 1 hour, washed, dried and then probed with peroxidase-conjugated goat anti-human IgG (Fab)$_2$ fragment specific antibody (Jackson ImmunoResearch Lab, West Grove, Pa.). The membrane was washed several times with TBS/0.05% Tween 20, before ECL Western blotting detection kit (Amersham Pharmacia Biotech UK Limited, Buckinghamshire, UK) was used to detect the protein band.

Western blots that were done after electrophoresis under non-reducing conditions showed a band of approximately 55 kD, a size in conformity with that of a Fab molecule. Similarly, Western blotting done following SDS-PAGE under reducing conditions yielded a band of 27-28 kD, a size expected of the Fd fragment. The Fab could be detected in 47 of the 48 cell lysates that were tested, albeit the degree of the intensity of the band varied.

Screening of Fabs for Their TAG-72 Binding Affinity by SPR

The expressed Fab molecules were screened for their immunoreactivity to the TAG-72 positive BSM, using BIAcore X instrument (Biacore, Piscataway, N.J.) for SPR measurements. All samples were run in duplicate over a sensor chip immobilized with 500 Resonance Units (RU) of BSM. Another sensor chip immobilized with 500 RU of BSA was used as a reference. Proteins were immobilized on carboxymethylated dextran CM5 chips (Biacore) by amine coupling using standard procedures (Johnsson et al., *Anal. Biochem.*, 198: 268, 1991; Schuck et al., 1999 Measuring protein interactions by optical biosensors. In: J. E. Coligan, B. M. Dunn, H. L. Ploegh, D. W. Speicher, and P. T. Wingfield (Eds.) Current Protocols in Protein Science. John Wiley & Sons, New York, Vol. 2, p. 20.2.1.) One hundred µl of each sample was applied at a flow rate of 20 µl/min and the dissociation was observed for 300 seconds. After the samples were washed with the running buffer, the surfaces were regenerated with 1 M CAPS buffer. The BIAeval 3.0.2 program was used to analyze the data. The BSA sensorgram was substracted from the corresponding BSM sensorgram and the Langmuir dissociation model was used to evaluate the off rate (k off).

Supernatants from all 48 cell lysates were analyzed for their reactivity to BSM. Since the Fabs were not purified, they were evaluated for their dissociation rates only. Fabs derived from the murine CC49, HuCC49V10 and human IgG (HuIgG) were included as controls. The dissociation rates of only 6 isolates were lower than that of HuCC49V10 (Table 5). They were characterized further, because these isolates are likely to have higher affinity for TAG-72.

TABLE 5

Dissociation rates of Fabs by Surface Plasmon Resonance

| Isolate | $K_{off}$ (1/s) |
| --- | --- |
| HuCC49V10-12 | $2.20 \times 10^{-4}$ |
| HuCC49V10-7 | $2.58 \times 10^{-4}$ |
| HuCC49V10-14 | $9.14 \times 10^{-4}$ |
| HuCC49V10-15 | $1.21 \times 10^{-4}$ |
| HuCC49V10-10 | $2.50 \times 10^{-3}$ |
| HuCC49V10-13 | $4.34 \times 10^{-4}$ |
| mCC49 | $1.04 \times 10^{-4}$ |
| HuCC49V10 | $1.07 \times 10^{-3}$ |
| HuIgG | $1.38 \times 10^{-2}$ |

The phagemids prepared from the cell pellets of the six isolates were used for the sequencing of the inserts encoding the variable regions of the light and heavy chain. DNA sequencing was carried out by the method of dideoxy-mediated chain termination. Amino acid sequences deduced from the nucleotide sequences showed substitutions in LCDR3 of all the six variants. These substitutions were limited to the positions 91, 93 and 94. Whereas, only one variant showed substitutions in HCDR2 (positions 52 and 58). Two variants showed inadvertent mutation in position 27b of the LCDR1 (Table 2).

Example 4

Expression of HuCC49V10 Variants in Insect Cells; Purification and Characterization of the Expressed Antibodies For further characterization of the variants, they were expressed in insect cells as whole antibodies, rather than as Fab fragments. To that end, expression constructs of the genes encoding the heavy and light chains of the variants were made in vectors containing promoters that are functional in insect cells. The variant antibodies were purified and studied for their relative antigen-binding affinity and their ability to bind to a cell surface antigen.

Figure 3A:
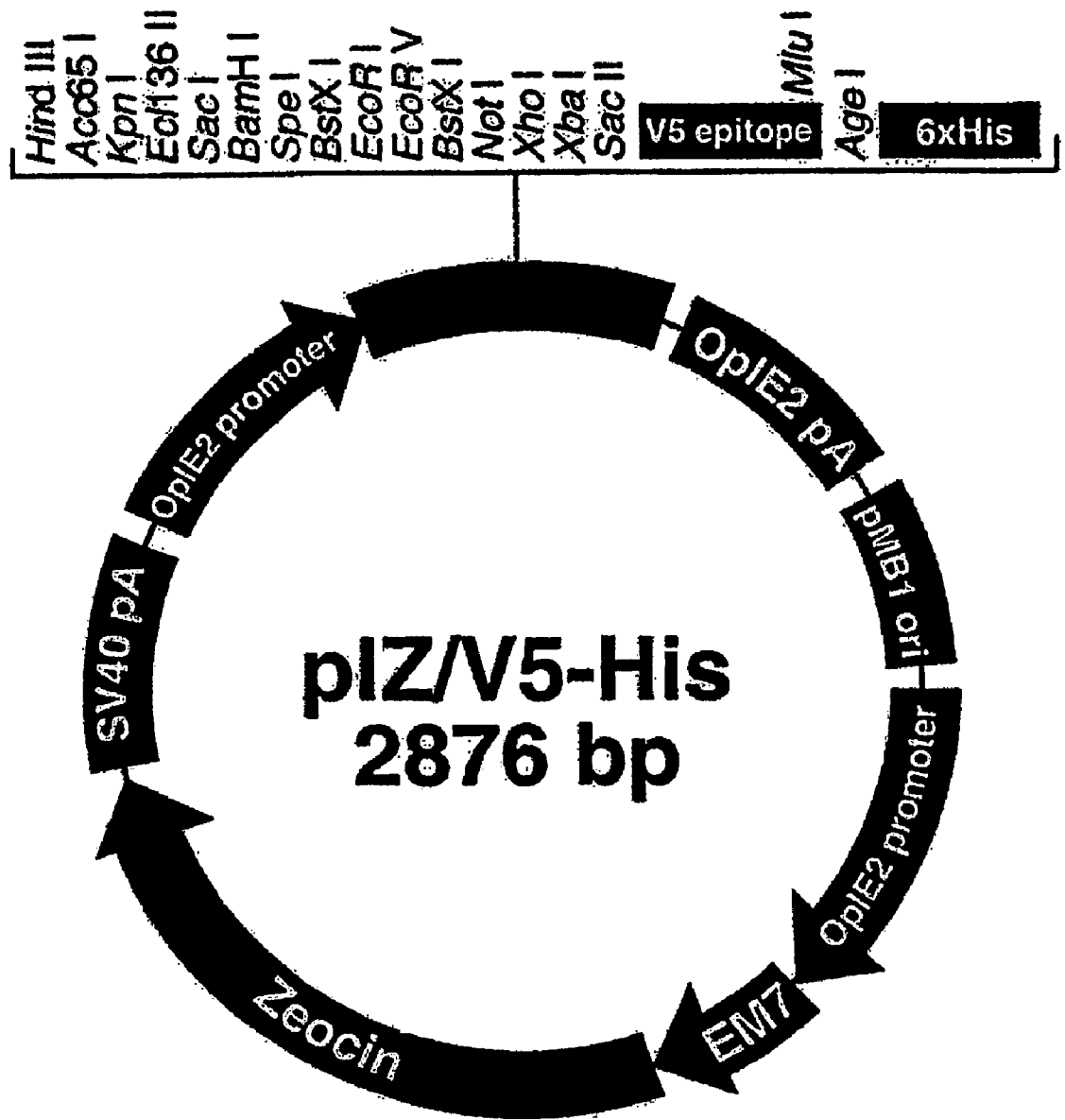
FIG. 3 is a schematic representation of the vectors pIZ/V5-His (FIG. 3A) and ppIB/V5-His (FIG. 3B) for the expression of proteins in insect cells.
Figure 3B:
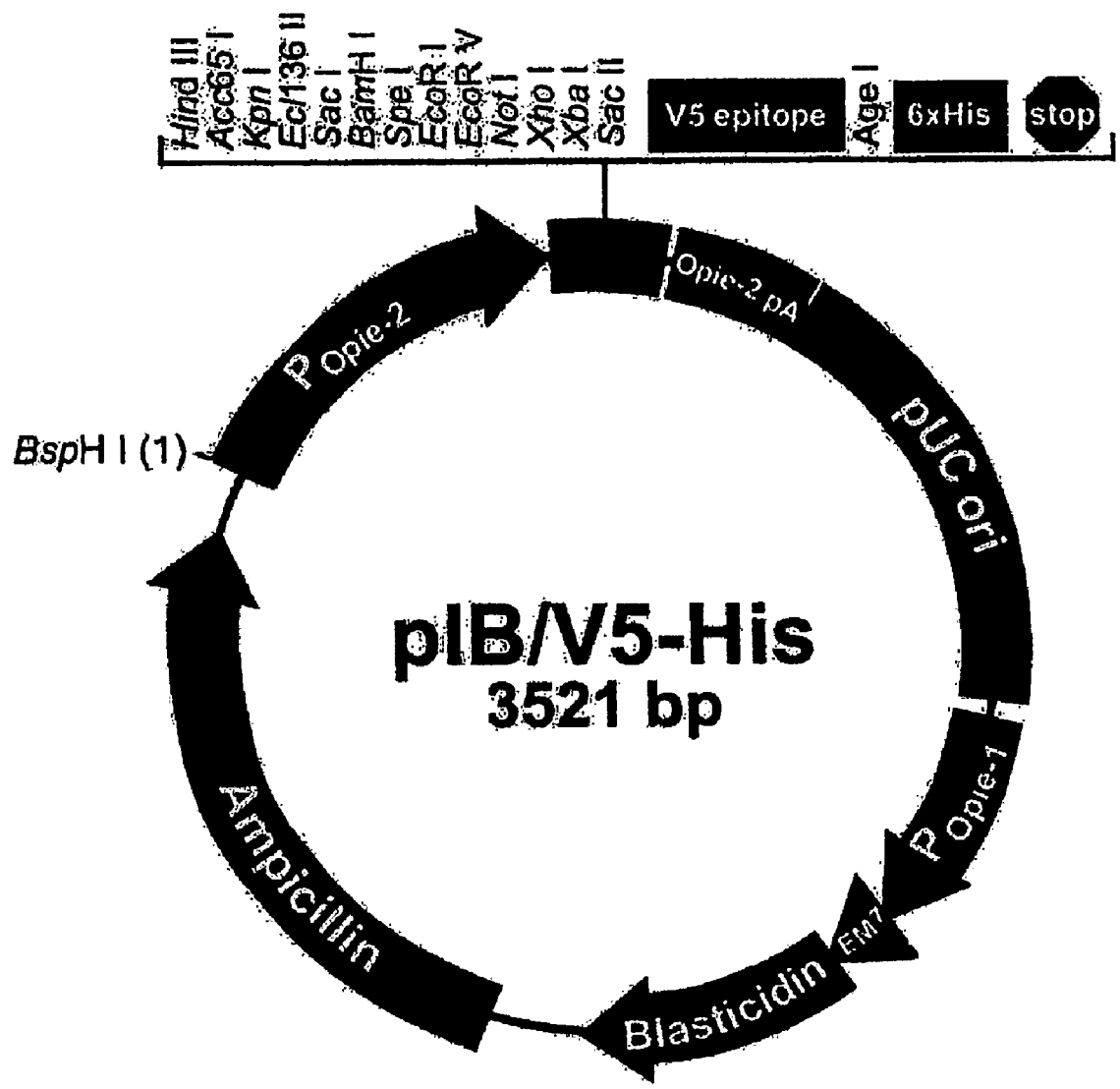

Expression Constructs of the Heavy and Light Chain Genes of the Variant Antibodies Two different vectors, pIZ/V5-His (FIG. 3A) and pIB/V5-His (FIG. 3B) (Invitrogen, Carlsbad, Calif.), carry the baculovirus immediate early promoter OpIE2 that drives the expression of heterologous proteins in lepidopteran insect cells, without requiring viral factors for its activation. A multiple cloning site located downstream from the promoter, in both vectors, facilitates cloning of the gene of interest to be expressed constitutively. A polyadenylation sequence placed immediately 3' to the multiple cloning site ensures efficient transcription termination and polyadenylation of mRNA. One vector, pIZ/V5-His, carries the Zeocin resistance gene, while the other, pIB/V5-His, carries the blasticidin resistance gene. These genes are used for selecting stable transfectants of the insect cell line.

The sequences encoding the light chain of the variants were assembled in the pIZ/V5-His vector. A series of genetic manipulations were required to provide a leader sequence for each of the genes encoding the light chain. Essentially, a 538 bp BsmA I/Blp I DNA fragment carrying the LCDR3 and/or LCDR1 mutation(s) and extending into the constant region was PCR amplified from each of the variants. This DNA fragment replaced the corresponding sequence from a pBluescript construct of the variant HuCC49V10-5, which carried the light chain gene of HuCC49V10 along with its leader sequence. The construct was digested with Sma I, for which a unique site was located immediately 3' to the insert, an Xba I linker was ligated to the DNA ends, and the insert was lifted as a Hind III/Xba I fragment of approximately 1 Kb. The insert was cloned downstream from the OpIE2 promoter at the Hind III/Xba I site.

The heavy chain expression constructs were made in the p13/V5-His vector. Since only one (varaint HuCC49V10-13) of the six variants showed any mutations in the HCDR2, the heavy chain construct of the variant HuCC49V10-8, which carried the heavy chain gene of the HuCC49V10 along with its leader sequence, was paired with the light chain constructs of the variants (variants HuCC49V10-7, HuCC49V10-10, HuCC49V10-12, HuCC49V10-14 and HuCC49V10-15) for the production of the variant antibodies. The gene encoding the heavy chain along with its leader was excised from the pBSc construct of the variant HuCC49V10-8 as a Hind III/Xho I fragment. The insert was cloned at the Hind III/Xho I site, downstream of the OpIE2 promoter in pIB/V5-His vector.

Construction of the expression vector containing the heavy chain of variant HuCC49V10-13 in the pIB/V5-His vector, while incorporating the eukaryotic leader sequence between the promoter and the gene, required some genetic manipulation. Essentially, an 85 bp Bcl I/Sca I fragment of variant HuCC49V10-8 was replaced with the corresponding DNA fragment of variant HuCC49V10-13 that carried the mutations in HCDR2. The manipulated insert was lifted from the construct as a Hind III/Xho I fragment and cloned in pIB/V5-His vector, downstream from the promoter.

Production of the Variant Antibodies and Their Immunoreactivity

To develop transfectomas secreting the HuCC49 variants, serum-free-adapted Sf9 insect cells (Gibco BRL) were used. Two million insect cells plated in each well of a 6-well plate were co-transfected with 10 µg each of the pIZ/V5-His-light chain and pIB/V5-His-heavy chain constructs, using Insectin-Plus Liposomes (Invitrogen) to mediate the transfections. After four days, the culture supernatants were harvested and tested, by ELISA, for Ig secretion and the reactivity of the secreted antibody to TAG-72. For isolating stable transfectants, selection medium containing 200 µg/ml of zeocin and 50 µg/1 ml of blasticidin was used. For ELISA assays, four-day harvests of culture supernatants were collected and frozen at −20° C., prior to use.

The ELISA assay for monitoring Ig production was carried out by a procedure described earlier (Example 3). To test the reactivity of the secreted antibody to TAG-72, 1 µg/well of BSM was coated on the individual wells of the 96-well polyvinyl microtiter plates. After saturation of the plates for 1 hour at 37° C. with milk blocking solution (KPL), 50 µl of diluted culture supernatants were added to the wells, in duplicate, followed by incubation at 37° C. for 1 hour. After a cycle of washings with the washing solution (KPL), 100 µl of peroxidase-conjugated anti-human IgG (Fcγ-fragment specific), diluted 1:3000 in milk diluent solution (KPL), was added to the plates and the incubation continued for an additional hour at 37° C. They were washed prior to the addition of 100 µl of TMB peroxidase substrate (KPL). The colorimetric reaction proceeded for 10 minutes at room temperature, before the addition of the stop solution (KPL). The absorbance was read at 450 nm.

Results of the ELISA of the culture supernatants for IgG showed that all the variants produced antibody. When the culture supernatants were assayed for their reactivity to TAG-72, it became evident that the antibodies produced by the variants were specific to TAG-72. When the ELISA was carried out using serially diluted supernatants, the results of the assay suggested that the antigen-binding reactivity of, at least two variant antibodies, HuCC49V10-14 and HuCC49V10-15, was either comparable to or exceeded that of the parental HuCC49V10, while the reactivity of variant HuCC49V10-13 was convincingly lower than that of HuCC49V10. Variant HuCC49V10-13 was not included in further studies.

Purification of the Variant Antibodies and Their SDS-PAGE Analysis

Figure 4A:
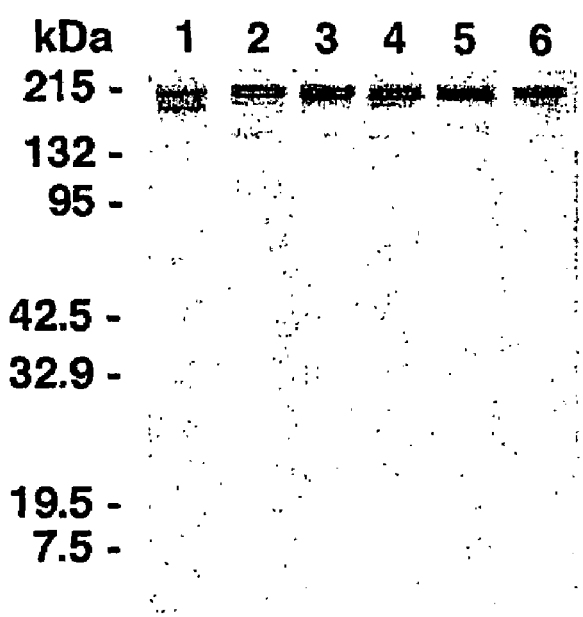
FIG. 4 is a set of digital images demonstrating SDS-PAGE analysis of purified HuCC49 and the variant antibodies derived from it under non-reducing (FIG. 4A) and reducing (FIG. 4B) conditions. Lane 1, HuCC49; lane 2, HuCC49V10; lane 3, HuCC49V10-7; lane 4, HuCC49V10-12, lane 5, HuCC49V10-14, lane 6, HuCC49V10-15 (lane designations are the same for FIGS. 4A and 4B).
Figure 4B:
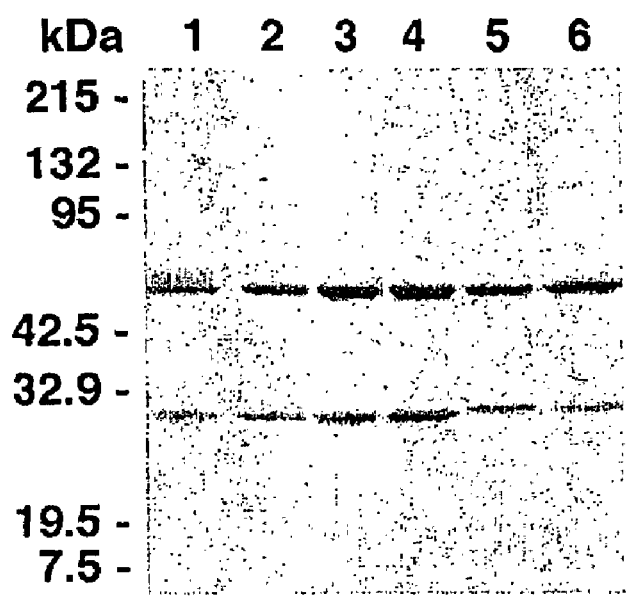

The supernatants collected from the cultures of the transfectomas producing the variant antibodies were centrifuged at 2,000×g for 10 minutes to remove cellular debris and loaded on a protein G agarose column (Gibco BRL). 0.1 M glycine hydrochloride pH 2.5 was used to elute the proteins bound to the column. The pH of the eluted material was immediately adjusted to 7.4 with 1.0 M Tris pH 8.0. The proteins were concentrated using a Centricon 30 (Amicon, Beverly, Mass.) and dialyzed in PBS buffer using Slide-A-Lyzer cassette (Pierce, Rockford, Ill.). The protein concentration was determined by the method of Lowry (Lowry et al., *J. Biol. Chem.*193: 265, 1951). The concentration of the variant antibodies ranged between 2-5 µg/ml of the culture supernatant. The purity of the eluted proteins was evaluated by SDS-PAGE, under reducing and non-reducing condition, using pre-cast 4-20% Tris-glycine gel (Novex, San Diego, Calif.) and Coomassie blue staining (Novex) visualization. Under non-reducing conditions (FIG. 4A) a protein band of approximately 160 kD was seen, while the reducing condition (FIG. 4B) yielded two protein bands of approximately 50-55 kD and approximately 25-28 kD, the sizes expected of the heavy and light chains of an IgG molecule.

Competition Radioimmunoassay (RIA)

The relative antigen-binding affinity of the variant antibodies was determined using competition RIA, as described earlier (Iwahashi et al., *Mol. Immunol.* 36:1079, 1999; Tamura et al., *J. Immunol.* 164:1432, 2000). Murine CC49, HuCC49 and HuIgG were included in the assay as positive and negative controls. Twenty five µl of serial dilutions of the antibodies, re-suspended in 1% BSA in PBS, were added to microtiter plates containing 10 ng of BSM saturated with 5% BSA in PBS. $^{125}$I-labeled HuCC49 (100,000 cpm in 25 µl of 1% BSA in PBS) was then added to each well. The assay was set up in triplicate. After an overnight incubation at 4° C., the plates were washed and counted in a γ-scintillation counter.

Figure 5:
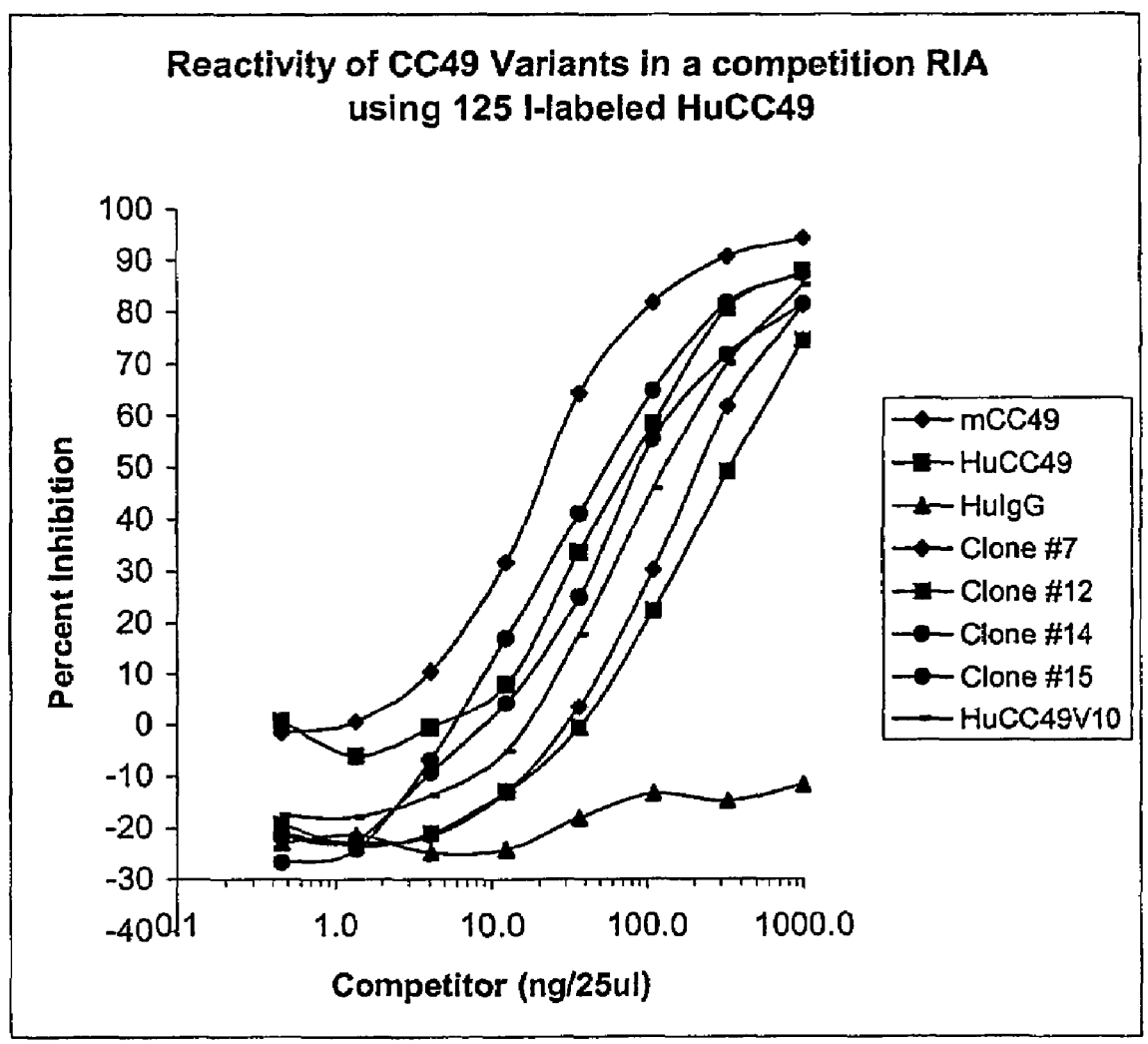
FIG. 5 is a graph demonstrating the reactivity of CC49 antibodies (identified by their symbols in the inset) in a competition RIA. Increasing concentrations of different antibodies were used to compete for the binding of $^{125}$I-labeled HuCC49 to the TAG-72 positive BSM.

The results of the competition assay (FIG. 5) show that all the antibodies, except the HuIgG control, were able to completely inhibit the binding of $^{125}$I-labeled HuCC49 to BSM. The competition profiles of the variants HuCC49V10-7 and HuCC49V10-12 were shifted to the right, while the profile of HuCC49V10-14 was shifted only slightly and that of HuCC49V 10-15 considerably to the left of the competition profile of the parental antibody HuCC49V10. Competition profiles, shown in FIG. 5, were used to calculate the amount of each unlabeled competitor required for 50% inhibition of the binding of $^{125}$I-labeled HuCC49 to BSM (Table 6). Compared to 150 ng of HuCC49V10, 220 ng and 350 ng of variants HuCC49V10-7 and HuCC49V10-12, respectively, were needed. In contrast, 92 ng of HuCC49V10-14 and only 58 ng of HuCC49V10-15 were required for 50% inhibition of the binding of $^{125}$I labeled HuCC49 to BSM. Thus, HuCC49V10-15 is approximately 3-fold better than that of HuCC49V10 antigen binding. The relative affinity constants ($K_a$) were calculated, from a range of competition experiments, using a modification of the Scatchard methods (Frankel and Gerhard, *Gene* 16:101, 1979). The $K_a$ values for HuCC49V10-14 were only comparable, while those for HuCC49V10-15 were approximately 50% higher than that of HuCC49V10.

TABLE 6

Relative affinity binding of CC49 antibodies

| CC49 antibody | Amount needed for 50% inhibition of the binding of $^{125}$I-labeled HuCC49 to BSM (ng) |
|---|---|
| mCC49: | 25 |
| HuCC49: | 78 |
| HuCC49V10: | 150 |
| HuCC49V10-7: | 220 |
| HuCC49V10-12: | 350 |
| HuCC49V10-14: | 92 |
| HuCC49V10-15: | 58 |

Flow Cytometric Analysis

Flow cytometric analysis was used to measure the binding of the HuCC49V10 variants to the TAG-72 expressed on the cell surface of a T cell line, Jurkat. The procedure for FACS analysis has been described (Guadagni et al., *Cancer Res.* 50:6248, 1990). In addition to the isotype matched antibody, HuIgG, used as a negative control, HuCC49 and chimeric CC49 were included as positive controls. To evaluate the ability of the variants to bind to cell-surface TAG-72, 1×10$^6$ Jurkat cells were resuspended in cold Ca$^{++}$ and Mg$^{++}$ free Dulbecco's PBS and incubated with the antibody to be tested for 30 minutes on ice. After one washing cycle, the cell suspension was stained with FITC-conjugated mouse anti-human antibody (Pharmingen) for 30 minutes on ice. A second washing cycle was performed before the samples were analyzed with a FACScan (Becton Dickinson, Mountain View, Calif.) using CellQuest for Macintosh. Data from the analysis of 10,000 cells were obtained.

Different concentrations of antibodies were used to compare their binding to the Jurkat cells expressing cell surface TAG-72. When 1.0 µg of each antibody was used, the percentage of gated cells, calculated after exclusion of irrelevant binding, was 27.8 for HuCC49V10, while for the variants HuCC49V10-14 and HuCC49V10-15, it was 43.7 and 68.1, respectively. Thus, the two variants show significantly better binding to the cells displaying TAG-72 on their surface. In contrast, the binding of the variants HuCC49V10-7 and HuCC49V10-12 was comparable to that of the parental HuCC49V10 (FIG. 6).

Example 5

Sera Reactivity of HuCC49V10 Variants

To assess the potential immunogenicity of the HuCC49V10 variants in patients, the variants were tested for their reactivity to sera stored from the adenocarcinoma patients in a phase I clinical trial (Mulligan et al., *Clin. Cancer Res.* 1: 1447, 1995). Patients in this clinical trial were administered $^{177}$Lu-labeled murine CC49 and were found to have anti variable region, including anti-idiotypic, antibodies to CC49 (Iwahashi et al., *Mol. Immunol.* 36: 1079, 1999; Tamura et al., *J. Immunol.* 164: 1432, 2000). Sera reactivity was determined by a highly sensitive Surface Plasmon Resonance (SPR)-based competition assay. This assay involves the use of a device (BIAcore X instrument) that monitors binding of the sera anti-idiotypic (or anti variable region) antibodies to HuCC49, and the inhibition of this binding by the variants. IC$_{50}$, the concentration of the competitor antibody required for 50% inhibition of the binding of the HuCC49 to the patient's serum was calculated by plotting the percent inhibition as a function of the competitor concentration. A higher IC$_{50}$ indicates a decreased reactivity to the serum suggesting potentially reduced immunogenicity of the competitor antibody (HuCC49 variant) in patients.

Immunoadsorption of Patients Sera

Sera from patient EA and DS from the phase I clinical trial were used to compare the reactivity of the variants HuCC49V10-14 and HuCC49V10-15 to that of the parental HuCC49V10. The sera, however, contain circulating TAG-72 antigen and anti-murine Fc antibodies that might interfere with the binding of the HuCC49 and its variants to the sera anti-idiotypic (anti variable) antibodies. To overcome this difficulty, TAG-72 and antibodies to murine Fc were removed from the sera by immunoadsorption prior to checking the sera reactivity. The procedure for immunoadsorption has been described (Iwahashi et al., *Mol. Immunol.* 36: 1079, 1999; Tamura et al., *J. Immunol.* 164: 1432, 2000). Essentially, a murine antibody, CC92, which reacts with an epitope of TAG-72 distinct from the one recognized by CC49 (Kuroki et al., *Cancer Res.* 50: 4872, 1990) was coupled to Reactigel (HW65F; Pierce, Rockford. IL) (Hearn et al., *J. Chomatogr.* 185: 463, 1979). Serum was added to an equivalent volume of the CC92 gel (wet-packed volume) and incubated overnight at 4° C. with end-over-end rotation. The samples were centrifuged at 1,000×g for 5 minutes and the supernatant was saved and stored.

SPR-Based Competition Assay

To test the sera reactivities of antibodies, SPR measurements were done with the BIAcore X instrument (described in Example 3) using carboxymethylated dextran chips CM5 (BIAcore, Piscataway, N.J.). Proteins were immobilized on the CM5 chips by amine coupling (Johnsson et al., *Anal. Biochem.* 198: 268, 1991). The dextran layer of the sensor chip was activated by injecting 35 μl of a mixture of N-ethyl-N'-(3 dimethylaminopropyl)carbodiimide hydrochloride and N-hydroxysuccinimide at a flow rate of 5 μl/min. Proteins diluted in 10 mM sodium acetate buffer (pH 5.0) at a concentration of 100 μg/ml were then injected until surfaces of 5000 resonance units (RUs) were obtained. The remaining reactive groups on the surfaces were blocked by injecting 35 μl of 1 M ethanolamine (pH 8.5).

To compare the sera reactivity of HuCC49, HuCC49V10 and its variants HuCC49V10-14 and HuCC49V10-15, competition experiments were done at 25° C. on a sensor chip containing HuCC49 in flow cell 1 and rabbit gamma globulin (BioRad, Hercules, Calif.) in flow cell 2 as a reference. A recently developed sample application technique was used (Abrantes et al., *Anal. Chem.* 73: 2828, 2001), in which the microfluidics control of the instrument was replaced by an externally installed computer-controlled syringe pump with stepping motor (model 402 from Gilson Inc., Middleton, Wis.). A tubing was inserted into the open port of the connector block in order to serve as an inlet port through which the sample can be aspirated, and the port previously designated as running buffer inlet was connected to the syringe pump (Abrantes et al., *Anal. Chem.* 73: 2828, 2001). The computer-controlled aspiration made it possible to use small sample volumes. Typically, the microfluidics system was rinsed and filled with running buffer (10 mM HEPES (pH 7.4), 150 mM NaCl, 3 mM EDTA and 0.005% Tween 20). This was followed by sequential aspiration of 2 μl of air, 0.3 μl of sample (preadsorbed serum±antibodies as competitors), 2 μl of air, 5-6 μl of sample, 2 μl of air, 0.3 μl of sample, and 2 μl of air into the inlet tubing at a rate of 20 μl/min. The sample was centered across the sensor surface and an oscillatory flow was applied at a rate of 20 μl/min. This flow ensures efficient mass transfer of the sample to the surface and allows for a very long contact time without net displacement of the sample. The binding was measured for 1000 seconds. After the unbound samples were removed from the surfaces by washing with running buffer using a flow rate of 100 μl/min, the surfaces were regenerated with a one-minute injection of 10 mM glycine (pH 2.0). The percent binding at each antibody concentration was calculated as follows: % binding=[slope of the signal obtained with competitor (serum+antibody)/slope of the signal obtained without competitor (serum only)]×100.

FIG. 7 shows the competition profiles generated by HuCC49 and different variants when they were used to compete with the HuCC49 immobilized on the sensor chip for binding to the anti-idiotypic (anti variable) antibodies to CC49 present in the sera of the patients EA and DS. For serum from patient DS, approximately one micromole of the variant HuCC49V10 is required for 50% inhibition of the binding of HuCC49 to the serum, while the variants HuCC49V10-14 and HuCC49V10-15 do not show any significant inhibition at this concentration. For serum from patient EA, approximately 20 nanomoles of the HuCC49V10 is needed for 50% inhibition of the binding of HuCC49 to the serum, whereas one micromole of each of the HuCC49V10-14 and HuCC49V10-15 variants cause less than 40% inhibition. Thus, the two mutants showed not only significantly higher antigen binding affinity than that of HuCC49V10, but they also showed much lower reactivity to sera from patients who showed an anti-idiotypic response to the parental CC49 antibody.

The improved affinity and the minimal sera reactivity of the variants HuCC49V10-14 and HuCC49V10-15 make them potentially much better clinical reagents than the variant HuCC49V 10.

Example 6

HuCC49V10-14 and HuCC46V10-15 Testing in Patients

Patients and Sample Collection

Patients with recurrent metastatic adenocarcinoma are assessed to determine the maximum tolerated dose of intravenously administered $^{177}$Lutetium radiolabeled HuCC49V10-14 and $^{177}$Lutetium radiolabeled HuCC49V10-15 (Mulligan, (1995) *Clin. Cancer Res.* 1: 1447-1454). Adenocarcinoma patients are given a test dose of 0.1 mg (intravenous bolus) of HuCC49V10-14 or HuCC49V10-15 and are observed for 30 minutes prior to administration of the $^{177}$Lu-labeled HuCC49V10-14 or $^{177}$Lu-labeled HuCC49V10-15. The radiolabeled antibodies are given as an intravenous infusion over the course of a one hour time interval. Blood samples are collected prior to and at the end of the infusion, as well as 0.5, 1 and 2 hours following the completion of the infusion. In addition, blood samples are collected daily over the subsequent 7 days. Patients return for a follow-up examination at 3, 6 or 8 weeks. Blood samples are again collected during these visits. Sera are separated and stored at −20° C.

Determination of Patient Humoral Response

The sera from the patients are evaluated for the presence of human anti-murine antibodies (HAMA) in response to radiolabeled HuCC49V10-14 or HuCC49V10-15 using the SPR-based assay described in Example 5, above. The sera is pre-absorbed with a CC92 monoclonal antibody that recognizes an epitope of TAG-72 which is different from the epitope recognized by the humanized CC49 monoclonal antibody. Pre-absorption using the CC92 antibody removes circulating TAG-72 from the sera. To monitor the sera-reactivity of the anti-variable antibodies in the pre-absorbed sera, HuCC49V10-14 or HuCC49V10-15 is coated on the surface of flow cell 1 and a reference protein (HuIgG1, bovine serum albumin, or rabbit gamma globulin) is immobilized on the surface of flow cell 2. A small, known volume of a patient serum sample us applied to each flow cell using the recently developed sample application technique described in Example 5 (Abrantes et al., *Anal. Chem.* 73:2828, 2001). Sensograms to flow cell 1 and flow cell 2 are generated and the response difference between the two cells is plotted for each serum sample, thus providing a measure of the anti-variable region response against HuCC49V10-14 or HuCC49V10-15 in each particular serum sample. Results indicate that the patients' sera have a minimal anti-variable region response against the HuCC49V10-14 and HuCC49V10-15 antibodies.

This disclosure provides humanized CC49 monoclonal antibodies. The disclosure further provides methods of diagnosing and treating tumors using these humanized CC49 antibodies. It will be apparent that the precise details of the methods described may be varied or modified without departing from the spirit of the described invention. We claim all such modifications and variations that fall within the scope and spirit of the claims below.

We claim:

1. A humanized CC49 antibody, deposited as ATCC Accession number PTA-4182 or ATCC Accession number PTA-4183.

2. A humanized CC49 antibody, comprising:
   four variable light framework regions and four variable heavy framework regions of a human antibody;
   a light chain complementarity determining region (L-CDR)1, a L-CDR2, a L-CDR3, a heavy chain complementarity determining region (H-CDR)1, a H-CDR2, and a H-CDR3;
   a non-conservative substitution of a first residue, wherein the first residue is in the L-CDR 3 of the antibody; and
   a substitution of a second residue, wherein the second residue is in any L-CDR or H-CDR of the antibody;
   wherein the non-conservative substitution of the first residue at position 91 is a tyrosine to proline substitution, the substitution of the second residue at position 27b is a valine to leucine substitution, the L-CDR1, L-CDR2, L-CDR3, H-CDR1, H-CDR2, and H-CDR3 are the parent HuCC49V10 antibody L-CDR1, L-CDR2, L-CDR3, H-CDR1, H-CDR2, and H-CDR3, respectively, and the humanized CC49 antibody has a high binding affinity for TAG-72 and is minimally immunogenic, compared to HuCC49V10, deposited as ATCC Accession No. PTA-5416.

3. A humanized CC49 antibody, comprising:
   a light chain complementarity determining region (L-CDR)1, a L-CDR2, and a L-CDR3, a heavy chain complementarity determining region (H-CDR)1, a H-CDR2, and a H-CDR3, all of a parent CC49 antibody, wherein the L-CDR3 of the humanized CC49 antibody or of an antigen binding fragment of the humanized CC49 antibody comprises a non-conservative amino acid substitution at position 91 and has a high binding affinity for TAG-72, compared to the parent CC49 antibody, wherein the parent CC49 antibody is HuCC49V10, deposited as ATCC Accession No. PTA-5416.

4. The humanized CC49 antibody of claim 3, wherein the non-conservative substitution is a tyrosine to proline substitution.

5. A humanized CC49 antibody, comprising:
a light chain complementarity determining region (L-CDR)1, a L-CDR2, and a L-CDR3, a heavy chain complementarity determining region (H-CDR)1, a H-CDR2, and a H-CDR3, all of a parent CC49 antibody, wherein the L-CDR3 of the humanized CC49 antibody or of an antigen binding fragment of the humanized CC49 antibody comprises a tyrosine to proline substitution at position 91 and has a high binding affinity for TAG-72, compared to the parent CC49 antibody, wherein the parent CC49 antibody is HuCC49V10, deposited as ATCC Accession No. PTA-5416.

6. The antibody of claim 5, wherein the high binding affinity is at least about $1.2 \times 10^{-8}$M.

7. The antibody of claim 5, wherein the humanized CC49 antibody is minimally immunogenic.

8. The antibody of claim 5, wherein the humanized CC49 antibody further comprises an effector molecule.

9. The antibody of claim 8, wherein the effector molecule is a detectable label.

10. A pharmaceutical composition comprising a therapeutically effective amount of the antibody of claim 5 in a pharmaceutically acceptable carrier.

11. A humanized CC49 antibody, comprising:
four variable light framework regions and four variable heavy framework regions of a human antibody;
a light chain complementarity determining region (L-CDR)1, a L-CDR2, and a L-CDR3 of the parent HuCC49V10 antibody, a heavy chain complementarity determining region (H-CDR)1, a H-CDR2, and a H-CDR3 of the parent HuCC49V10 antibody;
a non-conservative substitution of a residue at position 91 in the L-CDR3 of the antibody; and
a substitution of a residue at position 27b of L-CDR1 of the antibody;
wherein the humanized CC49 antibody has a high binding affinity for TAG-72 and is minimally immunogenic, compared to a parent HuCC49V10 antibody, deposited as ATCC Accession No. PTA-5416.

12. The humanized CC49 antibody of claim 11, wherein the substitution at position 91 is a proline to tyrosine substitution and the substitution at position 27b is a valine to leucine substitution.

13. A humanized CC49 antibody, comprising:
four variable light framework regions and four variable heavy framework regions of a human antibody;
a light chain complementarity determining region (L-CDR)1, a L-CDR2, and a L-CDR3 of the parent HuCC49V10antibody, a heavy chain complementarity determining region (H-CDR)1, a H-CDR2, and a H-CDR3 of the parent HuCC49V10 antibody;
a tyrosine to proline substitution at position 91 in the L-CDR3 of the antibody; and
a valine to leucine substitution at position 27b of L-CDR1 of the antibody;
wherein the humanized CC49 antibody has a high binding affinity for TAG-72 and is minimally immunogenic, compared to a parent HuCC49V10 antibody, deposited as ATCC Accession No. PTA-5416.

14. The antibody of claim 13, wherein the humanized CC49 antibody further comprises an effector molecule.

15. The antibody of claim 14, wherein the effector molecule is a detectable label.

16. A pharmaceutical composition comprising a therapeutically effective amount of the antibody of claim 13 in a pharmaceutically acceptable carrier.

17. A method of detecting a TAG-72-expressing tumor in a subject, comprising:
contacting a sample from the subject in vivo or in vitro with the antibody of claim 5 for a sufficient amount of time to form an immune complex; and
detecting the presence of the immune complex, wherein the presence of the immune complex demonstrates the presence of the TAG-72-expressing tumor.

18. The method of claim 17, wherein the tumor is a colorectal tumor, a gastric tumor, a pancreatic tumor, a breast tumor, a lung tumor, an adenocarcinoma, or an ovarian tumor.

19. The method of claim 17, wherein the antibody further comprises an effector molecule.

20. The method of claim 19, wherein the effector molecule is a detectable label.

21. A method of detecting a TAG-72-expressing tumor in a subject, comprising:
contacting a sample from the subject in vivo or in vitro with the antibody of claim 13 for a sufficient amount of time to form an immune complex; and
detecting the presence of the immune complex, wherein the presence of the immune complex demonstrates the presence of the TAG-72-expressing tumor.

22. The method of claim 21, wherein the tumor is a colorectal tumor, a gastric tumor, a pancreatic tumor, a breast tumor, a lung tumor, an adenocarcinoma, or an ovarian tumor.

23. The method of claim 21, wherein the antibody further comprises an effector molecule.

24. The method of claim 23, wherein the effector molecule is a detectable label.

25. A method of treating a subject having a tumor that expresses TAG-72, comprising administering to the subject a therapeutically effective amount of the antibody of claim 1, wherein administering the therapeutically effective amount of the antibody inhibits the growth of the tumor or reduces the size of the tumor, thereby treating the subject.

26. The method of claim 25, wherein the administration of a therapeutically effective amount of the antibody does not elicit a human anti-murine antibody response in a subject.

27. The method of claim 25, wherein the antibody further comprises an effector molecule.

28. The method of claim 27, wherein the effector molecule is a toxin or a radioactive isotope.

29. A method of treating a subject having a tumor that expresses TAG-72, comprising administering to the subject a therapeutically effective amount of the antibody of claim 2, wherein administering the therapeutically effective amount of the antibody inhibits the growth of the tumor or reduces the size of the tumor, thereby treating the subject.

30. A method of treating a subject having a tumor that expresses TAG-72, comprising administering to the subject a therapeutically effective amount of the antibody of claim 3, wherein administering the therapeutically effective amount of the antibody inhibits the growth of the tumor or reduces the size of the tumor, thereby treating the subject.

31. A method of treating a subject having a tumor that expresses TAG-72, comprising administering to the subject a therapeutically effective amount of the antibody of claim 5, wherein administering the therapeutically effective amount of the antibody inhibits the growth of the tumor or reduces the size of the tumor, thereby treating the subject.

32. A method of treating a subject having a tumor that expresses TAG-72, comprising administering to the subject a therapeutically effective amount of the antibody of claim 11, wherein administering the therapeutically effective amount of the antibody inhibits the growth of the tumor or reduces the size of the tumor, thereby treating the subject.

33. A method of treating a subject having a tumor that expresses TAG-72, comprising administering to the subject a therapeutically effective amount of the antibody of claim 13, wherein administering the therapeutically effective amount of the antibody inhibits the growth of the tumor or reduces the size of the tumor, thereby treating the subject.

34. A pharmaceutical composition comprising a therapeutically effective amount of the antibody of claim 1 in a pharmaceutically acceptable carrier.

35. A pharmaceutical composition comprising a therapeutically effective amount of the antibody of claim 2 in a pharmaceutically acceptable carrier.

36. A pharmaceutical composition comprising a therapeutically effective amount of the antibody of claim 3 in a pharmaceutically acceptable carrier.

37. A pharmaceutical composition comprising a therapeutically effective amount of the antibody of claim 11 in a pharmaceutically acceptable carrier.

38. The antibody of claim 1, wherein the humanized CC49 antibody further comprises an effector molecule.

39. The antibody of claim 38, wherein the effector molecule is a detectable label, a toxin, or a radioactive isotope.

40. The antibody of claim 2, wherein the humanized CC49 antibody further comprises an effector molecule.

41. The antibody of claim 40, wherein the effector molecule is a detectable label, a toxin, or a radioactive isotope.

42. The antibody of claim 3, wherein the humanized CC49 antibody further comprises an effector molecule.

43. The antibody of claim 42, wherein the effector molecule is a detectable label, a toxin, or a radioactive isotope.

44. The antibody of claim 11, wherein the humanized CC49 antibody further comprises an effector molecule.

45. The antibody of claim 44, wherein the effector molecule is a detectable label, a toxin, or a radioactive isotope.

46. A method of detecting a TAG-72-expressing tumor in a subject, comprising:
   contacting a sample from the subject in vivo or in vitro with the antibody of claim 1 for a sufficient amount of time to form an immune complex; and
   detecting the presence of the immune complex, wherein the presence of the immune complex demonstrates the presence of the TAG-72-expressing tumor.

47. A method of detecting a TAG-72-expressing tumor in a subject, comprising:
   contacting a sample from the subject in vivo or in vitro with the antibody of claim 2 for a sufficient amount of time to form an immune complex; and
   detecting the presence of the immune complex, wherein the presence of the immune complex demonstrates the presence of the TAG-72-expressing tumor.

48. A method of detecting a TAG-72-expressing tumor in a subject, comprising:
   contacting a sample from the subject in vivo or in vitro with the antibody of claim 3 for a sufficient amount of time to form an immune complex; and
   detecting the presence of the immune complex, wherein the presence of the immune complex demonstrates the presence of the TAG-72-expressing tumor.

49. A method of detecting a TAG-72-expressing tumor in a subject, comprising:
   contacting a sample from the subject in vivo or in vitro with the antibody of claim 11 for a sufficient amount of time to form an immune complex; and
   detecting the presence of the immune complex, wherein the presence of the immune complex demonstrates the presence of the TAG-72-expressing tumor.

* * * * *

UNITED STATES PATENT AND TRADEMARK OFFICE
CERTIFICATE OF CORRECTION

| | | |
|---|---|---|
| PATENT NO. | : 7,569,673 B2 | Page 1 of 1 |
| APPLICATION NO. | : 10/519580 | |
| DATED | : August 4, 2009 | |
| INVENTOR(S) | : Kashmiri et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 794 days.

Signed and Sealed this

Fourteenth Day of December, 2010

David J. Kappos
*Director of the United States Patent and Trademark Office*

SEQUENCE LISTING

<160> NUMBER OF SEQ ID NOS: 16

<210> SEQ ID NO 1
<211> LENGTH: 31
<212> TYPE: DNA
<213> ORGANISM: Artificial sequence
<220> FEATURE:
<223> OTHER INFORMATION: primer

<400> SEQUENCE: 1
tgagcggcac agagctcgac atcgtgatga g         31

<210> SEQ ID NO 2
<211> LENGTH: 26
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (14)..(14)
<223> OTHER INFORMATION: s is a g or c
<220> FEATURE:
<221> NAME/KEY: misc_feature
<222> LOCATION: (15)..(15)
<223> OTHER INFORMATION: h is a, c, or t
<220> FEATURE:
<221> NAME/KEY: misc_feature
<222> LOCATION: (16)..(16)
<223> OTHER INFORMATION: k is g or t

<400> SEQUENCE: 2
agctataata ctgshkacaa taatag         26

<210> SEQ ID NO 3
<211> LENGTH: 26
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (15)..(15)
<223> OTHER INFORMATION: b is g, t, or c
<220> FEATURE:
<221> NAME/KEY: misc_feature
<222> LOCATION: (16)..(16)
<223> OTHER INFORMATION: n is a, g, c or t

<400> SEQUENCE: 3
ggggatagct atagbnctgc tgacaa         26

<210> SEQ ID NO 4
<211> LENGTH: 26
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (14)..(14)
<223> OTHER INFORMATION: s is g or c
<220> FEATURE:
<221> NAME/KEY: misc_feature
<222> LOCATION: (15)..(16)
<223> OTHER INFORMATION: n is a, g, c or t

<400> SEQUENCE: 4
tgaggggata gctsnnatac tgctga         26

```
<210> SEQ ID NO 5
<211> LENGTH: 26
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (14)..(14)
<223> OTHER INFORMATION: s is g or c
<220> FEATURE:
<221> NAME/KEY: misc_feature
<222> LOCATION: (15)..(16)
<223> OTHER INFORMATION: n is a, g, c or t

<400> SEQUENCE: 5
agctgagggg atasnnataa tactgc                                          26

<210> SEQ ID NO 6
<211> LENGTH: 26
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (14)..(14)
<223> OTHER INFORMATION: s is g or c
<220> FEATURE:
<221> NAME/KEY: misc_feature
<222> LOCATION: (15)..(16)
<223> OTHER INFORMATION: n is a, g, c or t

<400> SEQUENCE: 6
cgaagctgag gggsnngcta taatac                                          26

<210> SEQ ID NO 7
<211> LENGTH: 26
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (14)..(14)
<223> OTHER INFORMATION: s is g or c
<220> FEATURE:
<221> NAME/KEY: misc_feature
<222> LOCATION: (15)..(16)
<223> OTHER INFORMATION: n is a, g, c or t

<400> SEQUENCE: 7
cagcgccgaa gctsnnggga tagcta                                          26

<210> SEQ ID NO 8
<211> LENGTH: 58
<212> TYPE: DNA
<213> ORGANISM: Artificial sequence
<220> FEATURE:
<223> OTHER INFORMATION: primer

<400> SEQUENCE: 8
gcgccgtcta gaattaacac tctcccctgt tgaagctctt tgtgacgggc gaactcag       58

<210> SEQ ID NO 9
<211> LENGTH: 32
<212> TYPE: DNA
<213> ORGANISM: Artificial sequence
<220> FEATURE:
```

<223> OTHER INFORMATION: primer

<400> SEQUENCE: 9
gcccgtacca tggcccaggt ccagctggtg ca                          32

<210> SEQ ID NO 10
<211> LENGTH: 25
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (12)..(12)
<223> OTHER INFORMATION: s is g or c
<220> FEATURE:
<221> NAME/KEY: misc_feature
<222> LOCATION: (13)..(14)
<223> OTHER INFORMATION: n is a, g, c or t

<400> SEQUENCE: 10
cggggagaga asnntccaat ccact                                  25

<210> SEQ ID NO 11
<211> LENGTH: 24
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (11)..(11)
<223> OTHER INFORMATION: s is g or c
<220> FEATURE:
<221> NAME/KEY: misc_feature
<222> LOCATION: (12)..(13)
<223> OTHER INFORMATION: n is a, g, c or t

<400> SEQUENCE: 11
cgtttccggg snngaaatat ccaa                                   24

<210> SEQ ID NO 12
<211> LENGTH: 24
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (11)..(11)
<223> OTHER INFORMATION: s is g or c
<220> FEATURE:
<221> NAME/KEY: misc_feature
<222> LOCATION: (12)..(13)
<223> OTHER INFORMATION: n is a, g, c or t

<400> SEQUENCE: 12
aatcatcgtt snnggagag aaat                                    24

<210> SEQ ID NO 13
<211> LENGTH: 24
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (12)..(13)
<223> OTHER INFORMATION: n is a, g, c or t

<400> SEQUENCE: 13

```
aaaaatcatc gnntccggga gaga                                              24

<210> SEQ ID NO 14
<211> LENGTH: 24
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (11)..(11)
<223> OTHER INFORMATION: s is g or c
<220> FEATURE:
<221> NAME/KEY: misc_feature
<222> LOCATION: (12)..(12)
<223> OTHER INFORMATION: n is a, g, c or t
<220> FEATURE:
<221> NAME/KEY: misc_feature
<222> LOCATION: (13)..(13)
<223> OTHER INFORMATION: h is a, c, or t

<400> SEQUENCE: 14
agtacttaaa snhatcgttt ccgg                                              24

<210> SEQ ID NO 15
<211> LENGTH: 24
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (11)..(11)
<223> OTHER INFORMATION: s is g or c
<220> FEATURE:
<221> NAME/KEY: misc_feature
<222> LOCATION: (12)..(13)
<223> OTHER INFORMATION: n is a, g, c or t

<400> SEQUENCE: 15
tctgtgagta snnaaaatca tcgt                                              24

<210> SEQ ID NO 16
<211> LENGTH: 28
<212> TYPE: DNA
<213> ORGANISM: Artificial sequence
<220> FEATURE:
<223> OTHER INFORMATION: primer

<400> SEQUENCE: 16
gcatgtacta gttttgcaca agatttgg                                          28
```